(12) United States Patent
Loscalzo et al.

(10) Patent No.: US 11,596,605 B2
(45) Date of Patent: Mar. 7, 2023

(54) PARTICLES FOR DELIVERY OF PROTEINS AND PEPTIDES

(71) Applicant: The Brigham and Women's Hospital, Inc., Boston, MA (US)

(72) Inventors: Joseph Loscalzo, Dover, MA (US); Ying-Yi Zhang, Quincy, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 588 days.

(21) Appl. No.: 16/322,669

(22) PCT Filed: Aug. 1, 2017

(86) PCT No.: PCT/US2017/044928
§ 371 (c)(1),
(2) Date: Feb. 1, 2019

(87) PCT Pub. No.: WO2018/026833
PCT Pub. Date: Feb. 8, 2018

(65) Prior Publication Data
US 2021/0244668 A1     Aug. 12, 2021

Related U.S. Application Data

(60) Provisional application No. 62/369,412, filed on Aug. 1, 2016, provisional application No. 62/371,306, filed on Aug. 5, 2016, provisional application No. 62/374,639, filed on Aug. 12, 2016.

(51) Int. Cl.
| | |
|---|---|
| *A61K 9/16* | (2006.01) |
| *A61K 47/61* | (2017.01) |
| *A61K 47/69* | (2017.01) |
| *A61K 38/18* | (2006.01) |
| *A61K 38/19* | (2006.01) |
| *A61K 38/20* | (2006.01) |
| *A61K 38/47* | (2006.01) |

(52) U.S. Cl.
CPC ......... *A61K 9/1676* (2013.01); *A61K 9/1652* (2013.01); *A61K 38/185* (2013.01); *A61K 38/1825* (2013.01); *A61K 38/1866* (2013.01); *A61K 38/1875* (2013.01); *A61K 38/195* (2013.01); *A61K 38/204* (2013.01); *A61K 38/47* (2013.01); *A61K 47/61* (2017.08); *A61K 47/6941* (2017.08)

(58) Field of Classification Search
CPC ............. A61K 9/1652; A61K 38/1866; A61K 47/61; A61K 9/5161
See application file for complete search history.

(56) References Cited

U.S. PATENT DOCUMENTS

| | | | |
|---|---|---|---|
| 8,043,833 B2 | 10/2011 | Schwartz et al. | |
| 8,349,910 B2 | 1/2013 | Carrico et al. | |
| 10,272,050 B2 | 4/2019 | Farokhzad et al. | |
| 2005/0163821 A1* | 7/2005 | Sung | A61F 2/915 424/426 |
| 2005/0226938 A1 | 10/2005 | Borbely et al. | |
| 2007/0087022 A1* | 4/2007 | Desai | A61K 9/107 514/449 |
| 2007/0092486 A1 | 4/2007 | Yesland | |
| 2007/0196497 A1 | 8/2007 | Pouliquen et al. | |
| 2008/0254078 A1* | 10/2008 | Kauper | A61K 9/1652 514/777 |
| 2008/0268063 A1* | 10/2008 | Jon | A61K 38/28 514/4.8 |
| 2011/0021745 A1* | 1/2011 | Santra | B82Y 5/00 977/773 |
| 2013/0195888 A1 | 8/2013 | Wang et al. | |

(Continued)

FOREIGN PATENT DOCUMENTS

| | | |
|---|---|---|
| CN | 101796075 | 8/2010 |
| CN | 102477172 | 5/2012 |
| CN | 102532580 | 7/2012 |

(Continued)

OTHER PUBLICATIONS

Yin et al., "SDF-α in glycan nanoparticles exhibits full activity and reduces pulmonary hypertension in rats," Biomacromolecules, Nov. 11, 2013, 14(11):4009-20.

Zaman et al., "Incorporation of SDF-1α into Pre-formed Dextran Sulfate and Chitosan Nanopaiticles." abstract only, The FASEB Journal, Apr. 2015, 29:LB645, 1 page.

EP Extended European Search Report in EP Appln, No. 17837552,3, dated Feb. 13, 2020, 16 pages.

Zaman et al., "Incorporation of heparin-binding proteins into pre-formed dextran sulfate-chitosan nanoparticles; Abstract LB645,"The FASEB Journal,, Apr. 2015, 29(1), 2 pages.

Amara et al., "Stromal cell-derived factor-lalpha associates with heparan sulfates through the first beta-strand of the chemokine," J. Biol. Chem., 1999, 274(34):23916-23925.

(Continued)

*Primary Examiner* — Andrew S Rosenthal
(74) *Attorney, Agent, or Firm* — Fish & Richardson P.C.

(57) ABSTRACT

The present application provides a method of making a particle comprising (i) obtaining a first solution comprising a negatively charged polysaccharide; (ii) obtaining a second solution comprising a positively charged polysaccharide; and (iii) mixing the first solution and the second solution to obtain a suspension comprising the particle. The present application also provides a method of making a therapeutic particle, comprising: (i) obtaining a solution comprising a therapeutic protein; (ii) obtaining a first suspension comprising the particle comprising a negatively charged polysaccharide and a positively charged polysaccharide, and (iii) mixing the solution of the therapeutic protein and the first suspension to obtain a second suspension comprising the therapeutic particle. The present application also provides particles (e.g., therapeutic particles) prepared by any one of the disclosed methods, as well as the compositions comprising such particles, and methods of treating a disease or condition using such particles and compositions.

16 Claims, 23 Drawing Sheets

(56) References Cited

U.S. PATENT DOCUMENTS

| | | |
|---|---|---|
| 2013/0266634 A1 | 10/2013 | Lin et al. |
| 2019/0022581 A1* | 1/2019 | Ba .......................... B32B 27/06 |

FOREIGN PATENT DOCUMENTS

| | | |
|---|---|---|
| JP | IP 2009215220 | 9/2009 |
| WO | WO 2014/130064 | 8/2014 |
| WO | WO 2016/040814 | 3/2016 |
| WO | WO 2016/061201 | 4/2016 |
| WO | WO 2016/065306 | 4/2016 |
| WO | WO 2017/062920 | 4/2017 |
| WO | WO 2018/026833 | 2/2018 |
| WO | WO 2018/144022 | 8/2018 |

OTHER PUBLICATIONS

Bader et al., "Preparation and characterization of SDF-1alpha-chitosan-dextran sulfate nanoparticles," J. Vis. Exp. 2015, (95):52323, 7 pages.

Chen et al., "Development of a chitosan-based nanoparticle formulation for delivery of a hydrophilic hexapeptide, dalargin," Biopolymers, 2008, 90(5):663-670.

Delair, "Colloidal polyelectrolyte complexes of chitosan and dextran sulfate towards versatile nanocarriers of bioactive molecules," Eur. J. Pharm. Biopharm., 78(1):10-18.

Digabriele et al., "Structure of a heparin-linked biologically active dimer of fibroblast growth factor," Nature, Jun. 1998, 393(6687):812-817.

Drogoz et al., "Towards biocompatible vaccine delivery systems: interactions of colloidal PECs based on polysaccharides with HIV-1 p24 antigen," Biomacromolecules, Feb. 2008, 9(2):583-591.

Ellis & Walton, "The estimation and recovery of dextran sulphates in biological fluids," J. Clin. Pathol., 1959, 12:467-472.

Faham et al., "Heparin structure and interactions with basic fibroblast growth factor," Science., Feb. 1996, 271(5252):1116-1120.

Fairbrother et al., "Solution structure of the heparin-binding domain of vascular endothelial growth factor," Structure, May 1998, 6(5):637-648.

Fermas et al., "Sulfated oligosaccharides (heparin and fucoidan) binding and dimerization of stromal cell-derived factor-1 (SDF-1/CXCL 12) are coupled as evidenced by affinity CE-MS analysis," Glycobiology, Sep. 2008, 18(12):1054-1064.

Ferrara, "Molecular and biological properties of vascular endothelial growth factor," J. Mol. Med., Jul. 1999, 77(7):527-543.

Gallagher, "Fell-Muir Lecture: Heparan sulphate and the art of cell regulation: a polymer chain conducts the protein orchestra," Int. J. Exp. Pathol., Aug. 2015, 96(4):203-231.

Ghadge et al., "SDF-1α as a therapeutic stem cell homing factor in myocardial infarction," Pharmacol. Ther., Oct. 2011, 129(1):97-108.

Grant et al., "Metachromatic activity of heparin and heparin fragments," Anal. Biochem., Feb. 1984, 137(1): 25-32.

Huang & Berkland, "Controlled release of repifermin from poly electrolyte complexes stimulates endothelial cell proliferation," J. Pharm. Sci., Jan. 2009, 98(1):268-280.

Huang et al., "Polyelectrolyte complexes stabilize and controllably release vascular endothelial growth factor," Biomacromolecules, May 2007, 8(5):1607-1614.

Kontermann, "Strategies for extended serum half-life of protein therapeutics," Curr. Opin. Biotechnol., Dec. 2011, 22(6):868-876.

Lauten et al., "Nanoglycan complex formulation extends VEGF retention time in the lung," Biomacromolecules, Aug. 2010, 11 (7):1863-1872.

Leader et al., "Protein therapeutics: a summary and pharmacological classification," Nature Review, Jan. 2008, 7(1):21-39.

Linhardt et al., "Separation of negatively charged carbohydrates by capillary electrophoresis," Journal of Chromatography, Jan. 1996, 720(1-2):323-335.

Mendelovits et al., "Improved colorimetric determination of chitosan concentrations by dye binding," Appl, Spectrosc., Aug. 2012, 66(8):979-982.

Morris et al., "Heparin-binding peptide as a novel affinity tag for purification of recombinant proteins," Protein Expr. Purif., Oct. 2016, 126:93-103.

Muller et al., "The cystine knot promotes folding and not thermodynamic stability in vascular endothelial growth factor," J. Biol. Chem., Aug. 2002, 277(45):43410-43416.

Muzzarelli, "Colorimetric determination of chitosan," Anal. Biochem. Apr. 1998, 260(2):255-257.

Ori et al., "A Systems Biology Approach for the Investigation of the Heparin/Heparan Sulfate Interactome," J. Biol. Chem., Jun. 2011, 286(22):19892-19904.

PCT International Search Report and Written Opinion in International Appln. No. PCT/US17/44928, dated Oct. 20, 2017, 17 pages.

Pubchem, CAS Registry No. 9011-18-1, "Dextran Sulfate Sodium," May 14, 2018, 4 pages.

PubChem,CAS Registry No. 9012-76-4, "CHITOSAN," Aug. 8, 2005, 22 pages.

Ricketts, "Dextran sulphate—a synthetic analogue of heparin," Biochem. J., Apr. 1952, 51(1):129-133.

Robinson et al., "VEGF165-binding sites within heparan sulfate encompass two highly sulfated domains and can be liberated by K5 lyase," J. Biol. Chem. Jan. 2006, 281(3):1731-1740.

Ruppert et al., "Human bone morphogenetic protein 2 contains a heparin-binding site which modifies its biological activity," Eur. J. Biochem., Apr. 1996, 237(1):295-302.

Sadir et al., "Characterization of the stromal cell-derived factor-1alpha-heparin complex," J. Biol. Chem., Nov. 2001, 276(11):8288-8296.

Sadir et al., "Heparan sulfate/heparin oligosaccharides protect stromal cell-derived factor-1 (SDF-1)/CXCL12 against proteolysis induced by CD26/dipeptidyl peptidase IV," J. Biol. Chem., Oct. 2004, 279(42):43854-43860.

Sarmento et al., "Oral bioavailability of insulin contained in polysaccharide nanoparticles," Biomacromolecules, Oct. 2007, 8(10):3054-3060.

Schlessinger et al., "Crystal structure of a ternary FGF-FGFR-heparin complex reveals a dual role for heparin in FGFR binding and dimerization," Mol. Cell. Sep. 2000, 6(3):743-750.

Sharma et al., "Stromal-derived factor-1/CXCR4 signaling: indispensable role in homing and engraftment of hematopoietic stem cells in bone marrow," Stem Cells Dev., Feb. 2011, 20(6):933-946.

Sharma et all., "Enhanced immune response against pertussis toxoid by IgA-loaded chitosan-dextran sulfate nanoparticles," J. Pharm, Sci. Jan. 2012, 101(1):233-244.

Stebler et al., "Primordial germ cell migration in the chick and mouse embryo: the role of the chemokine SDF-1/CXCL 12," Dev. Biol., Aug. 2004, 272:(2)351-361.

Takekoshi et al., "A locked, dimeric CXCL12 variant effectively inhibits pulmonary metastasis of CXCR4-expressing melanoma cells due to enhanced serum stability," Mol. Cancer Ther., Nov. 2012, 11(11):2516-2525.

Vallejo & Rinas, "Folding and dimerization kinetics of bone morphogenetic protein-2, a member of the transforming growth factor-beta family," The FEBS J., Jan. 2013, 280(l):83-92.

Van de Weert et al., "Complex coacervation of lysozyme and heparin: complex characterization and protein stability," Pharm. Res., Dec. 2004, 21(12):2354-2359.

Veldkamp et al., "The monomer-dimer equilibrium of stromal cell-derived factor-1(CXCL 12) is altered by pH, phosphate, sulfate, and heparin," Protein Sci., Apr. 2005, 14(4):1071-1081.

Xu & Esko, "Demystifying heparan sulfate-protein interactions," Annu. Rev. Biochem., Mar. 2014, 83:129-157.

Yin et al., "SDF-1alpha in glycan nanoparticles exhibits full activity and reduces pulmonary hypertension in rats," Biomacromolecules, Oct. 2013, 14(11):4009-4020.

Zaman et al., "Incorporation of heparin-binding proteins into preformed dextran sulfate-chitosan nanoparticles," Int. J. Nanomedicine, 11:6149-6159.

(56) References Cited

OTHER PUBLICATIONS

Zhao et al., "Binding affinities of vascular endothelial growth factor (VEGF) for heparin-derived oligosaccharides," Biosci. Rep., Feb. 2012, 32(1):71-81.
Zou et al., "Heparin-binding properties of lactoferrin and lysozyme," Comp. Biochem. Physiol. B., Dec. 1992, 103(4):889-895.
Wang et al., "Preparation and performance study of chitosan derivative hydrogel," Wuhan University of Technology, May 2011, 13 pages (with English abstract).

* cited by examiner

PARTICLES FOR DELIVERY OF PROTEINS AND PEPTIDES

CLAIM OF PRIORITY

This application is a § 371 national stage application of International Application No. PCT/US2017/044928, filed on Aug. 1, 2017, which claims the benefit of U.S. Provisional Application No. 62/374,639, filed Aug. 12, 2016; U.S. Provisional Application No. 62/371,306, filed Aug. 5, 2016; and U.S. Provisional Application No. 62/369,412, filed Aug. 1, 2016. The entire contents of the foregoing are hereby incorporated by reference.

STATEMENT AS TO FEDERALLY SPONSORED RESEARCH

This invention was made with Government support under Grant Nos. HL048743, HL061795, GM107618, and HL108630, awarded by National Institutes of Health (NIH). The Government has certain rights in the invention.

TECHNICAL FIELD

This invention relates to particles, compositions, methods of making, and methods of use thereof, and in particular to particles comprising therapeutic molecules such as therapeutic proteins.

BACKGROUND

Protein-based therapies are important in the treatment of diseases. Thus, there is a need to develop improved methods for the delivery of biomolecules such as proteins to patients via, e.g., the pulmonary, nasal, intravenous, parenteral, subcutaneous, and oral routes.

Numerous particle (e.g., nanoparticle (NP)) platforms have been developed for the delivery of proteins. However, the capability of existing NPs for protein delivery applications remains limited, e.g., due to low loading efficiency and uncontrollable release profiles.

The clinical translation of protein drugs and protein-delivering nanomedicines has been hindered due to difficulties in the development and manufacturing of protein-based therapeutics that must be overcome to achieve clinical translation. Limitations such as synthetic chemical coupling and formulation parameters such as homogenization, sonication, extrusion, and exposure to solvents often lead to the inactivation of biomolecules (e.g., therapeutic proteins). Safe and effective delivery of protein therapeutics to desired disease tissues remains a significant challenge. The particles, compositions and methods of the present disclosure help meet this need.

SUMMARY

In some embodiments, the present disclosure provides, inter alia, a method of making a therapeutic particle, the method comprising:
i) obtaining a solution comprising a therapeutic protein;
ii) obtaining a first suspension comprising a particle comprising a negatively charged polysaccharide and a positively charged polysaccharide, wherein the core of the particle comprises the positively charged polysaccharide; and
iii) mixing the solution of the therapeutic protein and the first suspension to obtain a second suspension comprising the therapeutic particle.

In some embodiments, the present disclosure provides a method of making a therapeutic particle, the method comprising:
i) obtaining a solution comprising a therapeutic protein;
ii) obtaining a first suspension comprising a particle comprising a negatively charged polysaccharide, a positively charged polysaccharide, and a divalent metal ion, wherein the positively charged polysaccharide is covalently crosslinked by a dicarboxylic acid linker in the core of the particle; and
iii) mixing the solution of the therapeutic protein and the first suspension to obtain a second suspension comprising the therapeutic particle.

In some embodiments, the first solution comprises an aqueous solvent. In some embodiments, the aqueous solvent is selected from water and buffered saline. In some embodiments, the buffered saline is Dulbecco's Phosphate-Buffered Saline (DPBS). In some embodiments, the concentration of the therapeutic protein in the solution is from about 2 nmol/ml to about 30 nmol/ml.

In some embodiments, the first suspension comprises an aqueous solvent.

In some embodiments, the molar ratio of the therapeutic protein in the solution to the monosaccharide units having a negatively charged functional group within the negatively charged polysaccharide in the particle is from about 0.25:100 to about 3:100.

In some embodiments, the mixing in step iii) is carried out by adding the solution of the therapeutic protein to the first suspension.

In some embodiments, the mixing is carried out at about 800 rpm.

In some embodiments, the mixing is carried out for about 20 min.

In some embodiments, the mixing in step iii) is followed by centrifugation and suspension of the resulting solids in a solution of a sugar alcohol to obtain the second suspension comprising the therapeutic particle.

In some embodiments, the mixing in step iii) is followed by centrifugation and suspension of the resulting solids in a solution of a sugar alcohol, DPBS, or saline to obtain the second suspension comprising the therapeutic particle.

In some embodiments, the solution of the sugar alcohol is an aqueous solution.

In some embodiments, the aqueous solution of sugar alcohol comprises about 2.5 wt. % of mannitol.

In some embodiments, the aqueous solution of sugar alcohol comprises about 5 wt. % of mannitol.

In some embodiments, the incorporation efficiency of the therapeutic protein in the particle is from about 90% to about 100%.

In some embodiments, the particle is a nanoparticle.

In some embodiments, the diameter of the nanoparticle is from about 300 nm to about 600 nm. In some embodiments, the diameter of the nanoparticle is from about 350 nm to about 500 nm. In some embodiments, the diameter of the nanoparticle is from about 300 nm to about 500 nm, according to measurements with a dynamic light scattering (DLS) method. In some embodiments, the diameter of the core of the nanoparticle is less than about 220 nm, as determined by passing the particle through a sterilization filtration membrane.

In some embodiments, the weight ratio of the negatively charged polysaccharide to the positively charged polysaccharide in the particle is from about 3:1 to about 5:1.

In some embodiments, the weight ratio of the negatively charged polysaccharide to the positively charged polysaccharide in the particle is about 4:1.

In some embodiments, the detectable amount of the negatively charged polysaccharide in the particle is about 80% of the total amount used for the particle preparation.

In some embodiments, the particle is negatively charged and the zeta-potential is from about −35 mV to about −50 mV. In some embodiments, the particle is negatively charged and the zeta-potential is from about −40 mV to about −45 mV.

In some embodiments, the negatively charged polysaccharide comprises a monosaccharide unit having a functional group that is negatively charged at physiological pH. In some embodiments, the functional group is selected from carboxylic acid (—C(=O)OH), sulfonic acid (—S(=O)$_2$(OH) or —SO$_3$H), and phosphonic acid (—P(=O)(OH)$_2$).

In some embodiments, the negatively charged polysaccharide is a glycosaminoglycan. In some embodiments, the glycosaminoglycan is selected from heparin, heparan sulfate, chondroitin sulfate, dermatan sulfate, keratan sulfate, and hyaluronic acid.

In some embodiments, the negatively charged polysaccharide is a glycan. In some embodiments, the glycan is dextran sulfate.

In some embodiments, the positively charged polysaccharide comprises a monosaccharide unit having a functional group that is positively charged at physiological pH. In some embodiments, the functional group is an amino group (—NH$_2$). In some embodiments, the positively charged polysaccharide is polyglucosamine. In some embodiments, the polyglucosamine is chitosan.

In some embodiments, the positively charged polysaccharide is crosslinked (e.g., covalently) in the core of the particle.

In some embodiments, the crosslinking agent is a dicarboxylic acid.

In some embodiments, the dicarboxylic acid is selected from the group consisting of glutaric acid, malic acid, succinic acid, and tartaric acid.

In some embodiments, the catalysts for the crosslinking are selected from the group consisting of 1-ethyl-3-(3-dimethylaminopropyl) carbodiimide (EDC), and N-hydroxysuccinimide (NHS).

In some embodiments, the crosslinked particle is selected for salt-resistance.

In some embodiments, the selection is made by incubation with 3-fold concentrated DPBS.

In some embodiments, the crosslinked particle is sterilized.

In some embodiments, the sterilization involves passing the particle through 0.22 m filtration membranes.

In some embodiments, the therapeutic protein is bound to the negatively charged polysaccharide in the therapeutic particle. In some embodiments, the therapeutic protein and the negatively charged polysaccharide are bound non-covalently. In some embodiments, the therapeutic protein comprises a heparin-binding domain.

In some embodiments, the heparin-binding domain is native to the therapeutic protein.

In some embodiments, the heparin-binding domain is tagged to the therapeutic protein during recombinant production of the therapeutic protein.

In some embodiments, the therapeutic protein is selected from a grown factor, a cytokine, an antibody, a hormone, a transmembrane protein, and an enzyme.

In some embodiments, the growth factor is selected from insulin-like growth factor, keratinocyte growth factor, platelet-derived growth factor (PDGFR), vascular endothelial growth factor (VEGF), epidermal growth factor receptor (EGFR) and fibroblast growth factor (FGF).

In some embodiments, the cytokine is selected from an interferon, a colony stimulating factor, a thymic stromal lymphopoietin and an interleukin.

In some embodiments, the enzyme is selected from agalsidase beta, imiglucerase, velaglucerase alfa, taliglucerase, alglucosidase alpha, laronidase, idursulfase, β-gluco-cerebrosidase, alglucosidase-α, laronidase, α-L-iduronidase, idursulphase, iduronate-2-sulphatase, galsulphase, agalsidase-β, human α-galactosidase A, α-1-proteinase, α-1-proteinase inhibitor, pancreatic enzyme, lactase, a glycoside hydrolases, lipase, amylase, protease, adenosine deaminase, alteplase, reteplase, tenecteplase, urokinase, collagenase, human deoxyribonuclease I, dornase-α, hyaluronidase, papain, asparaginase, rasburicase, streptokinase, anistreplase, and galsulfase.

In some embodiments, the therapeutic protein is selected from stromal cell-derived factor-1α (SDF-1α), vascular endothelial growth factor (VEGF), oncostatin M (OSM), ciliary neurotrophic factor (CNTF), bone morphogenetic protein-2 (BMP-2), basic fibroblast growth factor (FGF-2) and lysozyme.

In some embodiments, the therapeutic protein is selected from stromal cell-derived factor-1α (SDF-1α), vascular endothelial growth factor (VEGF), bone morphogenetic protein-2 (BMP-2), basic fibroblast growth factor (FGF-2) and lysozyme.

In some embodiments, the loading capacity of the particle with respect to the therapeutic protein is from about 0.25 nmol to about 3 nmol per 100 nmol of the monosaccharide unit having a negatively charged functional group within the negatively charged polysaccharide.

In some embodiments, the loading capacity of the particle with respect to the therapeutic protein is less than about 10% of the total amount of monosaccharide units having a negatively charged functional group within the negatively charged polysaccharide.

In some embodiments, the therapeutic protein is stromal cell-derived factor-1α (SDF-1α), the negatively charged polysaccharide is dextran sulfate, and the loading capacity of the particle with respect to SDF-1α is from about 1 nmol to about 3 nmol per 100 nmol of glucose sulfate units of dextran sulfate.

In some embodiments, the therapeutic protein is vascular endothelial growth factor (VEGF), the negatively charged polysaccharide is dextran sulfate, and the loading capacity of the particle with respect to VEGF is from about 0.6 nmol to about 1 nmol per 100 nmol of glucose sulfate units of dextran sulfate.

In some embodiments, the therapeutic protein is bone morphogenetic protein-2 (BMP-2), the negatively charged polysaccharide is dextran sulfate, and the loading capacity of the particle with respect to BMP-2 is from about 0.5 nmol to about 1 nmol per 100 nmol of glucose sulfate units of dextran sulfate.

In some embodiments, the therapeutic protein is basic fibroblast growth factor (FGF-2), the negatively charged polysaccharide is dextran sulfate, and the loading capacity of the particle with respect to FGF-2 is from about 1 nmol to about 2 nmol per 100 nmol of glucose sulfate units of dextran sulfate.

In some embodiments, the therapeutic protein is lysozyme, the negatively charged polysaccharide is dextran sulfate, and the loading capacity of the particle with respect to lysozyme is from about 1 nmol to about 2 nmol per 100 nmol of glucose sulfate units of dextran sulfate.

In some embodiments, the therapeutic particle comprises at least two therapeutic proteins. In some embodiments, the particle comprises stromal cell-derived factor-1α (SDF-1α) and vascular endothelial growth factor (VEGF).

In some embodiments, the particle comprising a negatively charged polysaccharide and a positively charged polysaccharide wherein the core of the particle comprises the positively charged polysaccharide, is made by a method comprising:

i) obtaining a first solution comprising a negatively charged polysaccharide;

ii) obtaining a second solution comprising a positively charged polysaccharide; and iii) mixing the first solution and the second solution to obtain a suspension comprising the particle comprising a negatively charged polysaccharide and a positively charged polysaccharide wherein the core of the particle comprises the positively charged polysaccharide.

In some embodiments, the particle comprising a negatively charged polysaccharide and a positively charged polysaccharide wherein the core of the particle comprises the positively charged polysaccharide, is made by a method comprising:

iii) obtaining a first solution comprising a negatively charged polysaccharide;

iv) obtaining a second solution comprising a positively charged polysaccharide;

v) obtaining a third solution comprising a divalent ion, vi) mixing the three solutions to obtain a suspension comprising the particle, vii) precipitating the particle in the suspension by centrifugation, viii) suspending the particle in buffered water at pH of about 7.0, ix) mixing the particle with a dicarboxylic acid, EDC and NHS to achieve crosslinking of the positively charged polysaccharide in the core of the particle, x) selecting a salt-resistant crosslinked particle with 3-fold concentrated DPBS, and xi) filtering of the particle through 0.22 micrometer PVDF membrane for the purpose of sterilization and final size selection.

In some embodiments, the first solution is an aqueous solution.

In some embodiments, the aqueous solution in the first solution is water.

In some embodiments, the concentration of the negatively charged polysaccharide in the first solution is about 1 mg/ml.

In some embodiments, the second solution is an aqueous solution.

In some embodiments, the aqueous solution in the second solution is about 0.2% acetic acid in water.

In some embodiments, the concentration of the positively charged polysaccharide in the second solution is about 1 mg/ml.

In some embodiments, the weight ratio of the negatively charged polysaccharide to the positively charged polysaccharide is about 4:1.

In some embodiments, the mixing in step iii) is carried out by adding the second solution to the first solution.

In some embodiments, the mixing in step iii) is carried out at about 800 rpm.

In some embodiments, the mixing of the first solution and the second solution in step iii) is followed by addition of an aqueous solution of a metal salt to the mixture.

In some embodiments, the metal is selected from calcium, magnesium, barium, zinc and beryllium. In some embodiments, the metal is calcium. In some embodiments, the metal is zinc.

In some embodiments, the metal salt is $ZnSO_4$. In some embodiments, the concentration of $ZnSO_4$ in the aqueous solution of a metal salt is about 0.2 M. In some embodiments, the weight ratio of $ZnSO_4$ to the negatively charged polysaccharide is about 1.3:1.

In some embodiments, the addition of the aqueous solution of the metal salt to the mixture of step iii) is followed by the addition of an aqueous solution of a sugar alcohol to the mixture. In some embodiments, the sugar alcohol is mannitol. In some embodiments, the concentration of the sugar alcohol in the aqueous solution is about 15 wt. %. In some embodiments, the weight ratio of the sugar alcohol to the negatively charged polysaccharide is about 75:1.

In some embodiments, the mixing in step iii) is followed by centrifugation and suspension of the resulting solids in a solution of a sugar alcohol to obtain the second suspension comprising the particle.

In some embodiments, the sugar alcohol is mannitol.

In some embodiments, the concentration of the sugar alcohol in the aqueous solution is about 5 wt. %.

In some embodiments, the present disclosure also provides a therapeutic particle prepared by any one of the methods disclosed herein.

In some embodiments, the present disclosure also provides a particle comprising a negatively charged polysaccharide and a positively charged polysaccharide wherein the core of the particle comprises the positively charged polysaccharide, prepared by any one of the methods described hereon.

In some embodiments, the present disclosure also provides a pharmaceutical composition comprising a therapeutic particle as described herein, and a pharmaceutically acceptable carrier.

In some embodiments, the present disclosure also provides a method of treating a disease or condition in a subject in need thereof, the method comprising administering to the subject a therapeutically effective amount of the therapeutic particle as described herein, or the pharmaceutical composition thereof.

In some embodiments, the disease or condition is beneficially treated by the therapeutic protein in the therapeutic particle. In some embodiments, the disease or condition is cancer. In some embodiments, the disease or condition is inflammation, macular degeneration, or pulmonary hypertension.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1:
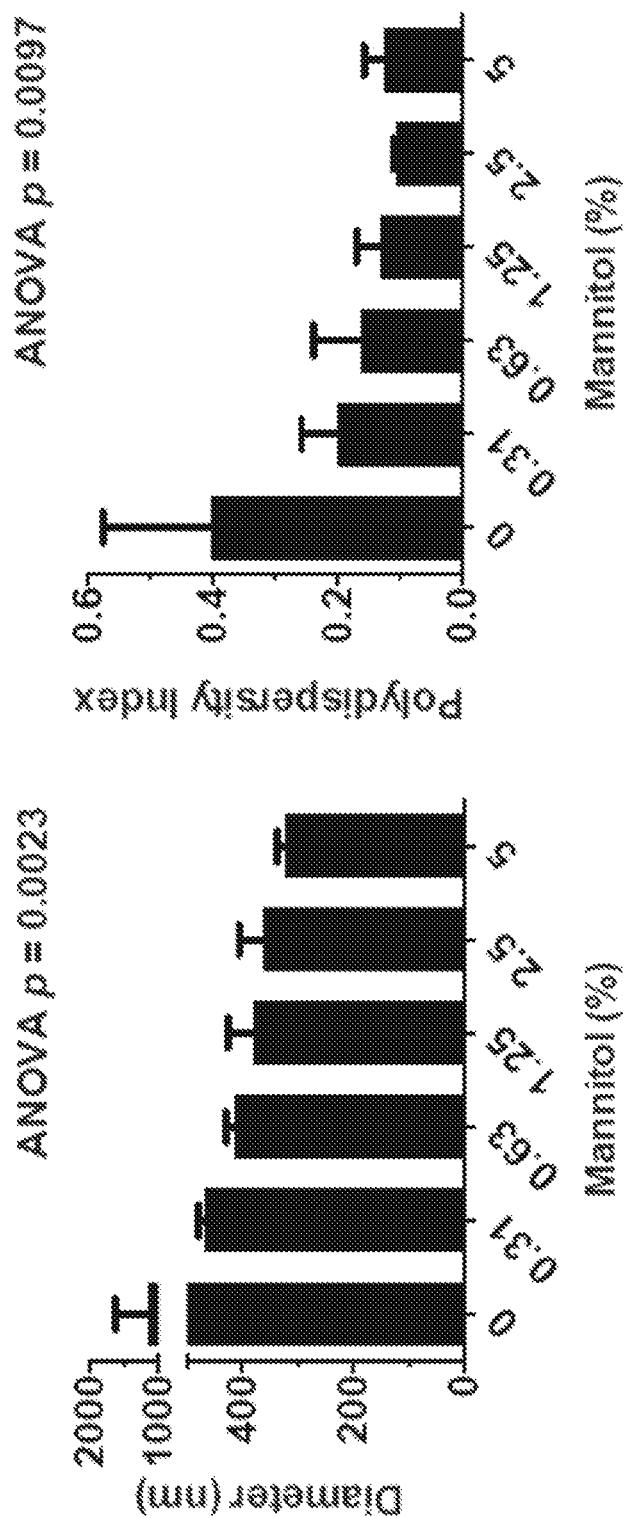
FIG. 1 is a bar graph showing effect of mannitol on the stability of dextran sulfate and chitosan (DSCS) nanoparticles during lyophilization. DSCS nanoparticles were suspended in mannitol solutions at the indicated concentrations and lyophilized. Prior to size measurement the particles were reconstituted with water to the original volume. Data represent the mean±SD of measurements from three preparations.

Particles of the Present Disclosure
Particles Comprising a Negatively Charged Polysaccharide and a Positively Charged Polysaccharide In some embodiments, the present disclosure provides a particle comprising a negatively charged polysaccharide and a positively charged polysaccharide, wherein the core of the particle comprises the positively charged polysaccharide. In some aspects of these embodiments, the outer shell (surface) of the particle does not comprise the positively charged polysaccharide. In other aspects of these embodiments, the core of the particle comprises at least about 70%, about 75%, about 80%, about 85%, about 90%, about 95%, or about 100% of the total amount of the positively charged polysaccharide.

In some embodiments, the present disclosure provides a particle comprising a negatively charged polysaccharide and a positively charged polysaccharide, wherein the outer shell (surface) of the particle comprises the negatively charged polysaccharide. In some aspects of these embodiments, the outer shell (surface) of the particle does not comprise the positively charged polysaccharide. In other aspects of these embodiments, the core of the particle comprises the positively charged polysaccharide. In other aspects of these embodiments, the core of the particle comprises at least about 70%, about 75%, about 80%, about 85%, about 90%, about 95%, or about 100% of the total amount of the positively charged polysaccharide.

In some embodiments, the present disclosure provides a particle comprising a core comprising a negatively charged polysaccharide and a positively charged polysaccharide; and an outer shell (surface) comprising the negatively charged polysaccharide. In some aspects of these embodiments, the outer shell (surface) of the particle does not comprise the positively charged polysaccharide. In other aspects of these embodiments, the core of the particle comprises at least about 70%, about 75%, about 80%, about 85%, about 90%, about 95%, or about 100% of the total amount of the positively charged polysaccharide.

Therapeutic Particles

In some embodiments, the present disclosure provides a therapeutic particle comprising a negatively charged polysaccharide and a positively charged polysaccharide, wherein the core of the particle comprises the positively charged polysaccharide, and further comprising at least one therapeutic protein (e.g., a therapeutic protein bound to the negatively charged polysaccharide). In some aspects of these embodiments, the outer shell (e.g., the surface of the therapeutic particle) does not comprise the positively charged polysaccharide. In other aspects of these embodiments, the core of the therapeutic particle comprises at least about 70%, about 75%, about 80%, about 85%, about 90%, about 95%, or about 100% of the total amount of the positively charged polysaccharide.

In some embodiments, the present disclosure provides a therapeutic particle comprising a negatively charged polysaccharide and a positively charged polysaccharide, wherein the outer shell (e.g., the surface of the therapeutic particle) comprises the negatively charged polysaccharide, and wherein at least one therapeutic protein is bound to the negatively charged polysaccharide. In some aspects of these embodiments, the outer shell (e.g., the surface of the therapeutic particle) does not comprise the positively charged polysaccharide. In other aspects of these embodiments, the core of the therapeutic particle comprises the positively charged polysaccharide. In other aspects of these embodiments, the core of the therapeutic particle comprises at least about 70%, about 75%, about 80%, about 85%, about 90%, about 95%, or about 100% of the total amount of the positively charged polysaccharide.

In some embodiments, the present disclosure provides a therapeutic particle comprising a core comprising a negatively charged polysaccharide and a positively charged polysaccharide; and an outer shell (e.g., surface of the therapeutic particle) comprising the negatively charged polysaccharide and at least one therapeutic protein. In some embodiments, the therapeutic protein is bound to the negatively charged polysaccharide.

In some embodiments, the negatively charged polysaccharide is bound to the positively charged polysaccharide through electrostatic interactions. In some embodiments, the amount of the negatively charged polysaccharide is sufficient to completely neutralize the positive charge of the positively charged polysaccharide.

Figure 11:
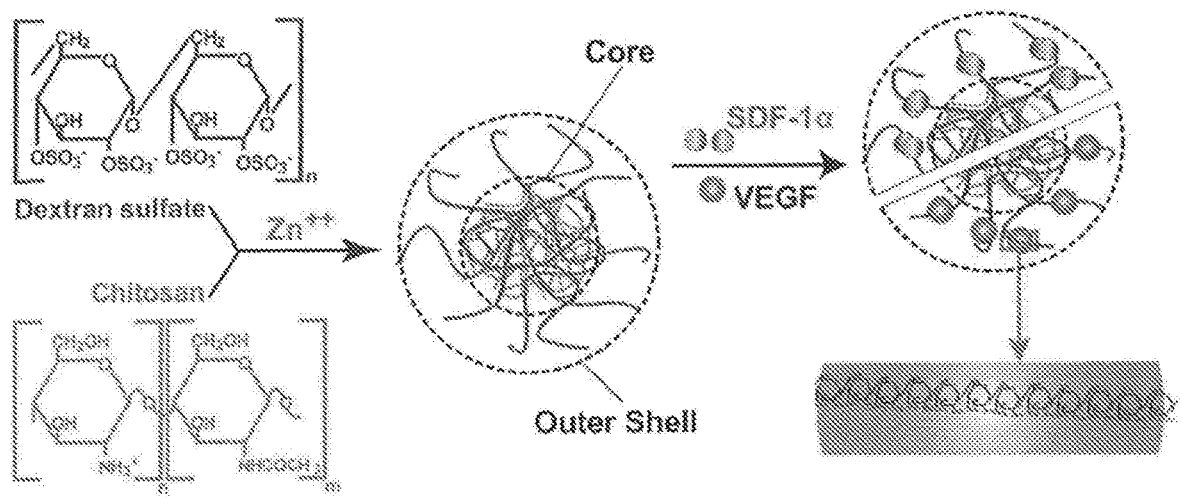
FIG. 11 is a diagram schematically showing formation of a DSCS nanoparticle.

Properties of the Particles (e.g., Therapeutic Particles) of the Present Disclosure Referring to FIG. 11, when the solution comprising a negatively charged polysaccharide (e.g., dextran sulfate) is mixed with a solution comprising the positively charged polysaccharide, the oppositely charged polysaccharide molecules react (e.g., through the electrostatic interactions) to form the particle comprising a core and an outer shell (surface of the particle). The positively charged polysaccharide is in the core of the particle, and the negatively charged polysaccharide, which is in excess of the positively charged polysaccharide, is both in the core and in the outer shell (surface) of the particle. This is possible because only the portion of the negatively charged polysaccharide molecule that reacted with the positively charged polysaccharide remains in the core of the particle, while the portion of the negatively charged polysaccharide molecule that did not react with the positively charged polysaccharide is located in the outer shell (surface) of the particle. In some embodiments, the outer shell (surface) of the particle comprises the unreacted negatively charged polysaccharide. The resultant particle comprising a negatively charged polysaccharide and a positively charged polysaccharide, wherein the core of the particle comprises the positively charged polysaccharide is further reacted with a therapeutic protein (e.g., any one of the therapeutic proteins described herein) to form a therapeutic particle as described herein. The therapeutic protein binds (e.g., non-covalently, as described herein) with residues of the negatively charged polysaccharide on the surface of the particle and remains in the outer shell (surface) of the therapeutic particle. In some embodiments, the core of the therapeutic particle does not comprise the therapeutic protein. In some embodiments, the outer shell (surface) of the particle comprises at least about 70%, about 75%, about 80%, about 85%, about 90%, about 95%, or about 100% of the total amount of the therapeutic protein.

In some embodiments, the particle or the therapeutic particle as described herein is a nanoparticle. In some embodiments, the size (e.g., diameter) of the nanoparticle is from about 300 nm to about 600 nm, or from about 350 nm to about 500 nm. In some embodiments, the diameter is from about 10 nm to about 800 nm, or from about 50 nm to about 600 nm, or from about 60 nm to about 550 nm. In some embodiments, the diameter is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, or about 700 nm.

In some embodiments, the weight ratio of the negatively charged polysaccharide to the positively charged polysaccharide in the particle is from about 1:1 to about 10:1. From about 2:1 to about 7:1, or from about 3:1 to about 5:1. In some embodiments, the weight ratio of the negatively charged polysaccharide to the positively charged polysaccharide in the particle is about 1:1, about 2:1, about 3:1, about 4:1, or about 5:1. In some embodiments, the weight ratio of the negatively charged polysaccharide to the positively charged polysaccharide in the particle is about 4:1.

In some embodiments, the detectable amount of the negatively charged polysaccharide in the particle is about 60%, about 70%, about 80%, or about 90% of the total amount used for the particle preparation of the particle.

In some embodiments, the particle is negatively charged and the zeta-potential is from about −35 mV to about −50 mV, or from about −40 mV to about −45 mV. In some embodiments, the zeta potential is from about −10 mV to about −100 mV, from about −20 mV to about −100 mV, from about −20 mV to about −80 mV, from about −30 mV to about −70 mV, or from about −40 mV to about −60 mV. In some embodiments, the zeta potential is about −10 mV, about −20 mV, about −30 mV, about −40 mV, about −45 mV, or about −50 mV.

In some embodiments, the particles present within a population, e.g., in a composition, can have substantially the same shape and/or size (i.e., they are "monodisperse"). For example, the particles can have a distribution such that no more than about 5% or about 10% of the particles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the particles. In some embodiments, the diameter of no more than 25% of the particles varies from the mean particle diameter by more than 150%, 100%, 75%, 50%, 25%, 20%, 10%, or 5% of the mean particle diameter. It is often desirable to produce a population of particles that is relatively uniform in terms of size, shape, and/or composition so that most of the particles have similar properties. For example, at least 80%, at least 90%, or at least 95% of the particles produced using the methods described herein can have a diameter or greatest dimension that falls within 5%, 10%, or 20% of the average diameter or greatest dimension. In some embodiments, a population of particles can be heterogeneous with respect to size, shape, and/or composition. In some embodiments, the polydispersity index is from about 0.01 to about 0.5, from about 0.05 to about 0.5, from about 0.1 to about 0.4, or from about 0.1 to about 0.3. In some embodiments, the polydispersity index is about 0.05, about 0.1, about 0.15, about 0.2, about 0.25 or about 0.3.

In some embodiments, the therapeutic protein is bound to the negatively charged polysaccharide in the particle non-covalently. In some embodiments, the therapeutic protein comprises a heparin-binding domain and is bound to the negatively charged polysaccharide in the particle through the heparin-binding domain. As used herein, the term "non-covalent" refers to an interaction between two or more components, wherein the bonds between the components are non-covalent bonds (i.e., no atom of one component shares a pair of electrons with an atom of another component). Non-covalent bonds include weak bonds such as hydrogen bonds, electrostatic effects, n-effects, hydrophobic effects or Van der Waals forces. In some embodiments, the non-covalent interaction between the therapeutic protein and negatively charged polysaccharide comprises hydrogen bonding, electrostatic interaction, hydrophobic interaction, and Van der Waals forces.

In some embodiments, any one of the particles described herein comprises a negatively charged polysaccharide comprising a monosaccharide unit comprising an —SO$_3$H functional group, and a positively charged polysaccharide comprising a monosaccharide unit comprising a —NH$_2$ functional group. In some embodiments, any one of the particles described herein comprises a glycan having an —SO$_3$H functional group, and a polyglucosamine comprising a —NH$_2$ functional group. In some embodiments, any one of the particles described herein comprises dextran sulfate (e.g., dextran sulfate sodium salt) and chitosan.

Negatively Charged Polysaccharide

The negatively charged polysaccharide may be a natural or synthetic polysaccharide comprising any number of monosaccharide residues (including any acyclic and/or cyclic forms and any possible stereoisomers) selected from allose, altrose, arabinose, erythrose, erythrulose, fructose, fucosamine, fucose, galactosamine, galactose, glucosamine, glucosaminitol, glucose, glyceraldehyde, glycerol, glycerone, gulose, idose, lyxose, mannosamine, mannose, psicose, quinovose, quinovosamine, rhamnitol, rhamnosamine, rhamnose, ribose, ribulose, sorbose, tagatose, talose, threose, xylose, xylulose, glucuronic acid and derivatives thereof. In some embodiments, monosaccharide residues in the negatively charged polysaccharide are selected from the group consisting of glucose, fructose, galactose, mannose, ribose, arabinose, xylose, N-acetylglucosamine, glucuronic acid, glucosamine, sialic acid, iduronic acid, galactosamine, and derivatives thereof. In some embodiments, negatively charged polysaccharide is acidic at neutral pH. In some embodiments, the negatively charged polysaccharide comprises a functional group that is negatively charged at physiological pH, e.g., acids, including carboxylic acids (carboxylates), sulfonic acids (sulfonates), sulfates, phosphates and phosphonates. That is, any number of monosaccharide units within the polysaccharide may be derivatized with —C(=O)OH, —S(=O)$_2$(OH) (i.e., —SO$_3$H), or —P(=O)(OH)$_2$ group. (In some embodiments, any one of these groups is negatively charged a the physiological pH). In some embodiments, the negatively charged polysaccharide is glycosaminoglycan, such as heparin, heparan sulfate, chondroitin sulfate, dermatan sulfate, keratan sulfate, or hyaluronic acid. In some embodiments, the negatively charged polysaccharide is a glycan such as dextran sulfate (e.g., dextran sulfate sodium salt, CAS Registry number 9011-18-1).

Positively Charged Polysaccharide

The positively charged polysaccharide may be a natural or synthetic polysaccharide comprising any number of monosaccharide residues (including any acyclic and/or cyclic forms and any possible stereoisomers) selected from allose, altrose, arabinose, erythrose, erythrulose, fructose, fucosamine, fucose, galactosamine, galactose, glucosamine, glucosaminitol, glucose, glyceraldehyde, glycerol, glycerone, gulose, idose, lyxose, mannosamine, mannose, psicose, quinovose, quinovosamine, rhamnitol, rhamnosamine, rhamnose, ribose, ribulose, sorbose, tagatose, talose, threose, xylose, xylulose, glucuronic acid and derivatives thereof. In some embodiments, monosaccharide residues in the positively charged polysaccharide are selected from the group consisting of glucose, fructose, galactose, mannose, ribose, arabinose, xylose, N-acetylglucosamine, glucosamine, N-acetylgalactosamine, galactosamine, and derivatives thereof.

In some embodiments, a net positive charge is provided by basic groups (e.g. amine, ammonium groups, or guanidinium groups) included in the positively charged polysaccharide. In some embodiments, the positively charged polysaccharide comprises a monosaccharide unit having a functional group that is positively charged at physiological pH. In some embodiments, a net positive charge is provided by amine and/or ammonium groups with which the monomeric monosaccharide units in the polysaccharide are derivatized. Any number of monosaccharide units within the positively charged polysaccharide may contain NH$_2$ group that may be positively charged at the physiological pH. In some embodiments, positively charged polysaccharide is basic at neutral pH. In some embodiments, the positively charged polysaccharide is polyglucosamine such as chitosan (See, e.g., CAS Registry number 9012-76-4).

In some embodiments, the positively charged polysaccharide is crosslinked. Suitable examples of crosslinking agents include dicarboxylic acids, such as oalic acid, malonic acid, malic acid (MA), succinic acid (SA), glutaric acid (GA), tartaric acid (TA), adipic acid, pimelic acid, suberic acid, azelaic acid, sebacic acid, brassilic acid or thapsic acid. In some embodiments, the crosslinking results in an amide bond formation between, e.g., amine groups in the positively charged polysaccharide and carboxyl groups in a dicarboxylic acid. The amide bond bridges the saccharide units of the polysaccharide together in the core of the particle. In some embodiments, the crosslinking of the polysaccharide in the core of the particle allows for increased salt stability of the particle as compared to a un-crosslinked particle that will form aggregates in physiological saline or body fluits owing to its nature of polyelectrolyte complex.

Therapeutic Proteins

In some embodiments, the therapeutic protein is an antibody, a hormone, a transmembrane protein, a growth factor, a cytokine, an enzyme, or a structural protein.

In some embodiments, the protein therapeutic is any one of protein therapeutics described in, e.g., Leader et al., *Nature Reviews* 2008, 7, 21-39, the disclosure of which is incorporated herein by reference in its entirety.

In some embodiments, the therapeutic protein is a heparin-binding protein.

Heparin-binding proteins are defined by their high affinity for heparin, which is commonly demonstrated by binding the proteins to heparin-Sepharose resin in ≥0.15 M NaCl. Many proteins, especially those mediating inter-cellular signaling, fall into this category. (See, e.g., Ori A, et al. J. Biol. Chem. 2011, 286 (22), 19892-19904.) The biological ligands of most of these proteins are heparan sulfate or sulfated glycosaminoglycans, which are present on the cell surface and in the extracellular matrix. A heparin-binding site or domain in the primary or tertiary structure of the proteins is responsible for heparin binding, which often includes a cluster of positively-charged amino acid residues (Lys, Arg, and His) that bind to heparin through electrostatic interaction. (See, e.g., Xu D, Esko J D. Demystifying heparan sulfate-protein interactions. Annu. Rev. Biochem. 2014; 83:129-157; and Gallagher J. Fell-Muir Lecture: Heparan sulphate and the art of cell regulation: a polymer chain conducts the protein orchestra. Int J Exp Pathol. August 2015; 96(4):203-231).

In some embodiments, the therapeutic protein comprises a heparin-binding domain. In some embodiments, the heparin-binding domain is native to the therapeutic protein. In other embodiments, the heparin-binding domain is tagged to the therapeutic protein during recombinant production of the therapeutic protein. The heparin-binding domain may be any one of the domains found in the heparin-binding proteins described, for example, in Ori A et al. J. Biol. Chem. 2011, 286 (22), 19892-19904, the disclosure of which is incorporated herein by reference. There are more than 435 heparin-binding proteins in humans, including many growth factors, cytokines, and proteins mediating intercellular communication. Other proteins or peptides (such as vaccines) could also be potentially delivered by DSCS NP and xNP, when a heparin-binding site is tagged to the terminal of the peptide sequence during protein synthesis The tagging of the heparin-binding domain may be carried out by any one of the procedures for recombinant protein production known in the art.

In some embodiments, the therapeutic protein is a cytokine, such as transforming growth factor-beta (TGF-beta), interferons (e.g., interferon-alpha, interferon-beta, interferon-gamma), colony stimulating factors (e.g., granulocyte colony stimulating factor (GM-CSF)), and thymic stromal lymphopoietin (TSLP). The interferon may be interferon-αcon1, interferon-alpha2a, interferon-α2b, interferon-αn3, interferon-β1a, or interferon-γ1b. The cytokine may be an interleukin, such as interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35. In some embodiments, the cytokine is selected from cytokine is selected from an interferon, a colony stimulating factor, a thymic stromal lymphopoietin and an interleukin.

In some embodiments, the therapeutic protein is a growth factor selected from insulin-like growth factor, keratinocyte growth factor, platelet-derived growth factor (PDGFR), vascular endothelial growth factor (VEGF), epidermal growth factor receptor (EGFR) and fibroblast growth factor (FGF).

In some embodiments, the therapeutic protein is a polypeptide hormone, such as amylin, anti-Müllerian hormone, calcitonin, cholecystokinin, corticotropin, endothelin, enkephalin, erythropoietin (EPO), darbepoetin, follicle-stimulating hormone, galanin, gastrin, ghrelin, glucagon, gonadotropin-releasing hormone, growth hormone-releasing hormone, hepcidin, human chorionic gonadotropin, growth hormone (GH), human growth hormone (hGH), inhibin, insulin, isophane insulin, insulin detemir, insulin glargine, pramlintide, pramlintide acetate, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, somatotropin, mecasermin, mecasermin rinfabate, human follicle-stimulating hormone, lutropin, teriparatide, exenatide, octreotide, dibotermin-α, bone morphogenetic protein 7, keratinocyte growth factor, platelet-derived growth factor, trypsin, nesiritide and vasopressin.

In some embodiments, the therapeutic protein is factor VIIa, factor VIII, factor IX, antithrombin III, protein C, drotrecogin-α, filgrastim, pegfilgrastim, sargramostim, Lepirudin, Bivalirudin, or oprelvekin. In some embodiments, the therapeutic protein is botulinum toxin type A, botulinum toxin type B. In some embodiments, the therapeutic protein is atacicept, abatacept, aflibercept, alefacept, belatacept, etanercept, sotatercept, romiplostim, or rilonacept.

In some embodiments, the therapeutic protein is an enzyme. In some embodiments, the enzyme is agalsidase beta, imiglucerase, velaglucerase alfa, taliglucerase, alglucosidase alfa, laronidase, idursulfase, β-gluco-cerebrosidase, alglucosidase-α, laronidase, α-L-iduronidase, idursulphase, iduronate-2-sulphatase, galsulphase, agalsidase-β, human α-galactosidase A, α-1-proteinase, α-1-proteinase inhibitor, pancreatic enzyme, lactase, a glycoside hydrolase (e.g. a lysozyme), lipase, amylase, protease, adenosine deaminase, alteplase, reteplase, tenecteplase, urokinase, collagenase, human deoxyribonuclease I, dornase-α, hyaluronidase, papain, asparaginase (e.g. L-Asparaginase), rasburicase, streptokinase, anistreplase, or galsulfase. In some embodiments, the therapeutic protein is albumin, human albumin, or immunoglobulin.

In some embodiments, the therapeutic protein is an antibody (e.g., monoclonal antibodies, e.g., bispecific monoclonal antibodies), including therapeutic antibodies. In some embodiments, the antibody is useful in treating cancer (e.g., abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, or zalutumumab).

In some embodiments, the antibody is useful in treating an inflammatory disease or condition (e.g., adalimumab, alemtuzumab, atlizumab, basiliximab, canakinumab, certolizumab, certolizumab pegol, daclizumab, muromonab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, or briakinumab). In some embodiments, the therapeutic protein is useful in treating infectious disease (e.g., enfuvirtide). In some embodiments, the therapeutic protein is abciximab, pegvisomant, crotalidae polyvalent immune Fab, digoxin immune serum Fab, ranibizumab, or ordenileukin diftitox.

In some embodiments, the therapeutic protein is selected from stromal cell-derived factor-1α (SDF-1α), vascular endothelial growth factor (VEGF), bone morphogenetic protein-2 (BMP-2), basic fibroblast growth factor (FGF-2) and lysozyme.

In some embodiments, the therapeutic protein is oncostatin M (OSM) or ciliary neurotrophic factor (CNTF). In some aspects of the embodiments, the therapeutic particle is useful in treating macular degeneration.

In some embodiments the therapeutic particle comprises SDF and VEGF therapeutic proteins. In some aspects of these embodiment, the particle is useful in treating pulmonary hypertension. In embodiments, the particle may be administered to a subject in combination with a stem cell.

In some embodiments, the loading capacity of the particle with respect to the therapeutic protein is from about 0.25 nmol to about 3 nmol of the therapeutic protein per 100 nmol of the monosaccharide unit having a negatively charged functional group within the negatively charged polysaccharide (e.g., the negatively charged polysaccharide on the surface of the particle). In some aspects of these embodiments, the loading capacity of the particle is from about 0.01 nmol to about 100 nmol, from about 0.1 nmol to about 50 nmol, from about 0.15 nmol to about 40 nmol, from about 0.2 nmol to about 30 nmol, from about 0.25 nmol to about 20 nmol, from about 0.25 nmol to about 10 nmol, from about 0.25 nmol to about 5 nmol, from about 0.25 nmol to about 2.5 nmol per 100 nmol of the monosaccharide unit having a negatively charged functional group within the negatively charged polysaccharide (e.g., the negatively charged polysaccharide on the surface of the particle). In some aspects of these embodiments, the loading capacity of the particle is about 0.1 nmol, about 0.15 nmol, about 0.2 nmol, about 0.25 nmol, about 0.5 nmol, about 0.75 nmol, about 1 nmol, about 1.25 nmol, about 1.5 nmol, about 2 nmol, about 2.5 nmol, about 3 nmol, about 3.5 nmol, about 4 nmol, about 5 nmol, about 10 nmol, about 20 nmol, about 50 nmol, or 100 nmol of the monosaccharide unit having a negatively charged functional group within the negatively charged polysaccharide (e.g., the negatively charged polysaccharide on the surface of the particle). In some embodiments, the loading capacity of the particle with respect to the therapeutic protein is less than about 30%, about 20%, about 15%, or about 10% of the total amount of monosaccharide units having a negatively charged functional group within the negatively charged polysaccharide.

In some embodiments, the proportion of the therapeutic protein relative to the therapeutic particle depends on the characteristics of the therapeutic protein, the properties of the therapeutic particle, and the application. In some embodiments, the therapeutic protein is loaded in the range from about 0.01% by weight to about 99% by weight of the total weight of the therapeutic particle. The therapeutic protein can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight.

In some embodiments, the therapeutic protein is a stromal cell-derived factor-1α (SDF-1α), the negatively charged polysaccharide is dextran sulfate, and the loading capacity of the particle with respect to SDF-1α is from about 1 nmol to about 3 nmol per 100 nmol of glucose sulfate units of dextran sulfate (e.g., dextran sulfate on the surface of the particle).

In some embodiments, the therapeutic protein is a vascular endothelial growth factor (VEGF), the negatively charged polysaccharide is dextran sulfate, and the loading capacity of the particle with respect to VEGF is from about 0.6 nmol to about 1 nmol per 100 nmol of glucose sulfate units of dextran sulfate (e.g., dextran sulfate on the surface of the particle).

In some embodiments, the therapeutic protein is a bone morphogenetic protein-2 (BMP-2), the negatively charged polysaccharide is dextran sulfate, and the loading capacity of the particle with respect to BMP-2 is from about 0.5 nmol to about 1 nmol per 100 nmol of glucose sulfate units of dextran sulfate (e.g., dextran sulfate on the surface of the particle).

In some embodiments, the therapeutic protein is a basic fibroblast growth factor (FGF-2), the negatively charged polysaccharide is dextran sulfate, and the loading capacity of the particle with respect to FGF-2 is from about 1 nmol to about 2 nmol per 100 nmol of glucose sulfate units of dextran sulfate (e.g., dextran sulfate on the surface of the particle).

In some embodiments, the therapeutic protein is a lysozyme, the negatively charged polysaccharide is dextran sulfate, and the loading capacity of the particle with respect to lysozyme is from about 1 nmol to about 2 nmol per 100 nmol of glucose sulfate units of dextran sulfate (e.g., dextran sulfate on the surface of the particle).

In some embodiments, the particle comprises at least two therapeutic proteins. In some embodiments, the particle comprises stromal cell-derived factor-1α (SDF-1α) and vascular endothelial growth factor (VEGF).

Further examples of useful therapeutic proteins can be found in U.S. Pat. Nos. 8,349,910; and 8,043,833; U.S. patent applications 2013/0195888; and 2007/0092486; and PCT WO 2014/130064, each of which is hereby incorporated by reference in its entirety.

Particles Prepared by a Process

In some embodiments, the present disclosure provides a particle comprising a negatively charged polysaccharide and a positively charged polysaccharide prepared by any one of the methods described herein.

In some embodiments, the present disclosure provides a therapeutic particle comprising a negatively charged polysaccharide, a positively charged polysaccharide, and a therapeutic protein bound to the negatively charged polysaccharide, prepared by any one of the methods described herein.

Methods of Making Particles of the Present Disclosure

Particles Comprising a Negatively Charged Polysaccharide and a Positively Charged Polysaccharide In some embodiments, the present disclosure provides a method of making a particle comprising a negatively charged polysaccharide and a positively charged polysaccharide, comprising:

xii) obtaining a first solution comprising a negatively charged polysaccharide;

xiii) obtaining a second solution comprising a positively charged polysaccharide; and xiv) mixing the first solution and the second solution to obtain a suspension comprising the particle.

In some embodiments, the core of the particle comprises the positively charged polysaccharide (e.g., at least 70%, at least 80%, at least 90%, or at least 100% of the positively charged polysaccharide is in the core of the particle).

In some embodiments, the first solution is an aqueous solution.

In some embodiments, the aqueous solvent in the first aqueous solution is water.

In some embodiments, the concentration of the negatively charged polysaccharide in the first solution is from about 0.1 mg/ml to about 10 mg/ml, from about 0.25 mg/ml to about 8 mg/ml, from about 0.5 mg/ml to about 5 mg/ml, or from about 0.5 mg/ml to about 2 mg/ml. In some embodiments, the concentration of the negatively charged polysaccharide in the first solution is about 0.5 mg/ml, about 1 mg/ml, about 1.5 mg/ml, or about 2 mg/ml. In some embodiments, the concentration of the negatively charged polysaccharide in the first solution is about 1 mg/ml.

In some embodiments, the second solution is an aqueous solution.

In some embodiments, the aqueous solvent in the second aqueous solution is from about 0.2% to about 0.5% acetic acid in water. In some embodiments, the aqueous solvent in the second aqueous solution is about 0.2% acetic acid in water.

In some embodiments, the concentration of the positively charged polysaccharide in the second solution is from about 0.1 mg/ml to about 10 mg/ml, from about 0.25 mg/ml to about 8 mg/ml, from about 0.5 mg/ml to about 5 mg/ml, or from about 0.5 mg/ml to about 2 mg/ml. In some embodiments, the concentration of the positively charged polysaccharide in the second solution is about 0.5 mg/ml, about 1 mg/ml, about 1.5 mg/ml, or about 2 mg/ml. In some embodiments, the concentration of the positively charged polysaccharide in the second solution is about 1 mg/ml.

In some embodiments, the weight ratio of the negatively charged polysaccharide from the first solution to the positively charged polysaccharide from the second solution is from about 1:1 to about 10:1, from about 2:1 to about 8:1, or from about 3:1 to about 5:1. In some embodiments, the weight ratio of the negatively charged polysaccharide to the positively charged polysaccharide is about 1:1, about 2:1, about 3:1, about 4:1 or about 5:1. In some embodiments, the weight ratio of the negatively charged polysaccharide to the positively charged polysaccharide is about 4:1.

In some embodiments, the mixing in step iii) is carried out by adding the second solution to the first solution. In some embodiments, the mixing in step iii) is carried out by adding the first solution to the second solution.

In some embodiments, the mixing in step iii) is carried out from about 400 rpm to about 1200 rpm, from about 500 rpm to about 1100 rpm, or from about 600 rpm to about 1000 rpm. In some embodiments, the mixing in step iii) is carried out at about 400 rpm, about 600 rpm, about 800 rpm or about 1000 rpm. In some embodiments, the mixing in step iii) is carried out at about 800 rpm.

In some embodiments, the mixing of the first solution and the second solution in step iii) is followed by addition of an aqueous solution of a metal salt to the mixture. In some embodiments the metal is selected from calcium, magnesium, barium, zinc and beryllium. In some embodiments, the metal is calcium. In some embodiments, the metal is zinc. In some embodiments, the metal salt is selected from $CaSO_4$, $CaCl_2$), $MgCl_2$, $MgSO_4$, $ZnCl_2$ and $ZnSO_4$. In some embodiments, the metal salt is $ZnSO_4$.

In some embodiments, the concentration of the metal salt in the aqueous solution of a metal salt is from about 0.01 M to about 1 M, from about 0.05 M to about 0.5 M, or from about 0.1 M to about 0.3 M. In some embodiments, the concentration of $ZnSO_4$ in the aqueous solution of a metal salt is from about 0.01 M to about 1 M, from about 0.05 M to about 0.5 M, or from about 0.1 M to about 0.3 M.

In some embodiments, the concentration of $ZnSO_4$ in the aqueous solution of a metal salt is about 0.05 M, about 0.1 M, about 0.15 M, about 0.2 M, about 0.25 M, or about 0.3 M. In some embodiments, the concentration of $ZnSO_4$ in the aqueous solution of a metal salt is about 0.2 M.

In some embodiments, the weight ratio of the metal salt to the negatively charged polysaccharide is from about 10:1 to about 1:10, from about 8:1 to about 1:2, from about 6:1 to about 1:1, from about 4:1 to about 1:1, or from about 2:1 to about 1:1.

In some embodiments, the weight ratio of $ZnSO_4$ to the negatively charged polysaccharide is from about 10:1 to about 1:10, from about 8:1 to about 1:2, from about 6:1 to about 1:1, from about 4:1 to about 1:1, or from about 2:1 to about 1:1. In some embodiments, the weight ratio of $ZnSO_4$ to the negatively charged polysaccharide is about 4:1, about 3:1, about 2:1, about 1.5:1, about 1.4:1, about 1.3:1, about 1.2:1, or about 1:1. In some embodiments, the weight ratio of $ZnSO_4$ to the negatively charged polysaccharide is about 1.3:1.

In some embodiments, the addition of the aqueous solution of the metal salt to the mixture of step iii) is followed by the addition of an aqueous solution of a sugar alcohol (e.g., mannitol, erythritol, sucrose, lactose, sorbitol, lactitol, glycerol, xylitol, inositol or volemitol) to the mixture.

In some embodiments, the sugar alcohol is mannitol.

In some embodiments, the concentration of the sugar alcohol in the aqueous solution is from about 1 wt. % to about 50 wt. %, from about 2 wt. % to about 40 wt. %, from about 3 wt. % to about 30 wt. %, or from about 5 wt. % to about 20 wt. %. In some embodiments, the concentration of the sugar alcohol in the aqueous solution is about 1 wt. %, about 2 wt. %, about 3 wt. %, about 5 wt. %, about 10 wt. %, about 15 wt. %, about 20 wt. %, about 25 wt. %, or about 30 wt. %. In some embodiments, the concentration of the sugar alcohol in the aqueous solution is about 15 wt. %.

In some embodiments, the weight ratio of the sugar alcohol to the negatively charged polysaccharide is from about 200:1 to about 1:1, from about 150:1 to about 10:1, from about 100:1 to about 20:1, or from about 90:1 to about 50:1. In some embodiments, the weight ratio of the sugar alcohol to the negatively charged polysaccharide is about 100:1, about 90:1, about 75:1, about 60:1, about 50:1, or about 30:1. In some embodiments, the weight ratio of the sugar alcohol to the negatively charged polysaccharide is about 75:1.

In some embodiments, the mixing in step iii) is followed by centrifugation and suspension of the resulting solids in a solution of a sugar alcohol to obtain the second suspension comprising the particle. In some aspects of these embodiments, the sugar alcohol is mannitol. In some aspects of these embodiments, the concentration of the sugar alcohol in the aqueous solution is from about 0.1 wt. % to about 25 wt. %, from about 0.5 wt. % to about 20 wt. %, from about 1 wt. % to about 15 wt. %, from about 2 wt. % to about 10 wt. %, or from about 3 wt. % to about 7 wt. %. In some aspects of these embodiments, the concentration of the sugar alcohol in the aqueous solution is about 1 wt. %, about 2 wt. %, about 3 wt. %, about 4 wt. %, about 4 wt. %, about 6 wt. %, or about 10 wt. %. In some aspects of these embodiments, the concentration of the sugar alcohol in the aqueous solution is about 5 wt. %.

In some embodiments, the particle s prepared by covalently crosslinking chitosan in the core of the particle with a dicarboxylic acid. In some embodiments, the particles comprising a negatively charged polysaccharide and a positively charged polysaccharide in the core of the particle is suspended in an aqueous buffer at about neutral pH. Suitable examples of aqueous buffers include HEPES [4-(2-hydroxyethyl)-1-piperazineethanesulfonic acid] buffered water at pH of about 7.0. In some embodiments, the suspension of the particle is admixed with a solution of a short chain dicarboxylic acid. Suitable examples of dicarboxylic acids include glutaric acid, malic acid, succinic acid, and tartaric acid. In some embodiments, the concentration of the dicarboxylic acid in the solution is from about 5 mM to about 30 mM. In some embodiments, the crosslinking reaction is carried out in the presence of 1-ethyl-3-(3-dimethylaminopropyl) carbodiimide (EDC, at a concentration of, e.g., about 20 to about 100 mM), and N-hydroxysuccinimide (NHS, at a concentration of, e.g., about 20 to about 100 mM). Suitable examples of crosslinking conditions include reacting the particle for about 16 h at about 25° C. In some embodiments, the particle with the crosslinked positively charged polysaccharide in the core is precipitated by centrifugation at about 15,000×g for about 15 min and washed with DPBS. In some embodiments, the crosslinked particle is further resuspended in 3×DPBS (3-fold high concentration of DPBS) for salt-resistance selection. In these embodiments, after 3 h incubation, aggregates in the suspension are precipitated by centrifugation at about 200×g for about 15 min, and the remaining particles are precipitated by a centrifugation at about 15,000×g for about 15 min. In some embodiments, the particles are then resuspended in DPBS, and filtered through PVDF membranes with pore size of 0.22 micrometer. In some embodiments, the filtration is conducted for the purpose of sterilization of the solution and final particle size selection.

Therapeutic Particles

In some embodiments, the present disclosure provides a method of making a therapeutic particle, the method comprising:
  i) obtaining a solution comprising a therapeutic protein;
  ii) obtaining a first suspension comprising a particle comprising a negatively charged polysaccharide and a positively charged polysaccharide (as described herein); and
  iii) mixing the solution of the therapeutic protein and the first suspension to obtain a second suspension to obtain the therapeutic particle.

In some embodiments, the core of the particle comprises the positively charged polysaccharide (e.g., at least 70%, at least 80%, at least 90%, or at least 100% of the positively charged polysaccharide is in the core of the particle).

In some embodiments, the first solution comprises an aqueous solvent.

In some embodiments, the aqueous solvent is selected from water and buffered saline. In some embodiments, the buffered saline is 50% Dulbecco's Phosphate-Buffered Saline (PBS).

In some embodiments, the concentration of the therapeutic protein in the solution is from about 0.1 nmol/ml to about 200 nmol/ml, from about 0.2 nmol/ml to about 150 nmol/ml, from about 0.3 nmol/ml to about 100 nmol/ml, from about 0.5 nmol/ml to about 80 nmol/ml, from about 0.75 nmol/ml to about 60 nmol/ml, from about 1 nmol/ml to about 60 nmol/ml, or from about 2 nmol/ml to about 30 nmol/ml. In some embodiments, the concentration of the therapeutic protein in the solution is from about 2 nmol/ml to about 30 nmol/ml. In some embodiments, the concentration of the therapeutic protein in the solution is about 0.1 nmol/ml, about 0.2 nmol/ml, about 0.3 nmol/ml, about 0.5 nmol/ml, about 0.75 nmol/ml, about 1 nmol/ml, about 1.25 nmol/ml, about 1.5 nmol/ml, about 1.75 nmol/ml, about 2 nmol/ml, about 3 nmol/ml, about 5 nmol/ml, about 7.5 nmol/ml, about 10 nmol/ml, about 15 nmol/ml, about 20 nmol/ml, about 25 nmol/ml, about 30 nmol/ml, about 40 nmol/ml, or about 50 nmol/ml.

In some embodiments the first suspension comprises an aqueous solvent. In some aspects of these embodiments, the aqueous solvent comprises a sugar alcohol (e.g., mannitol, erythritol, sucrose, lactose, sorbitol, lactitol, glycerol, xylitol, inositol or volemitol), and in particular mannitol, in a concentration from about 0.1 wt. % to about 25 wt. %, from about 0.2 wt. % to about 20 wt. %, from about 0.5 wt. % to about 10 wt. %, or from about 1 wt. % to about 5 wt. %, or in a concentration of about 0.5 wt. %, about 1 wt. %, about 1.5 wt. %, about 2 wt. %, about 2.5 wt. %, about 3 wt. %, about 4 wt. %, or about 5 wt. %.

In some embodiments, the molar ratio of the therapeutic protein in the solution to the monosaccharide units having a negatively charged functional group within the negatively charged polysaccharide in the particle is from about 0.01:100 to about 100:100, from about 0.05:100 to about 50:100, from about 0.1:100 to about 40:100, from about 0.2:100 to about 20:100, from about 0.2:100 to about 10:100, from about 0.2:100 to about 5:100. In some embodiments, the molar ratio of the therapeutic protein in the solution to the monosaccharide units having a negatively charged functional group within the negatively charged polysaccharide in the particle is from about 0.25:100 to about 3:100. In some embodiments, the molar ratio of the therapeutic protein in the solution to the monosaccharide units having a negatively charged functional group within the negatively charged polysaccharide in the particle is about 0.1:100, about 0.2:100, about 2.5:100, about 0.3:1000, about 0.5:100, about 1:100, about 2:100, about 3:100, or about 5:100.

In some embodiments, the mixing in step iii) is carried out by adding the solution of the therapeutic protein to the first suspension. In some embodiments, the mixing in step iii) is carried out by adding first suspension to the solution of the therapeutic protein.

In some embodiments, the mixing in step iii) is carried out from about 400 rpm to about 1200 rpm, from about 500 rpm to about 1100 rpm, or from about 600 rpm to about 1000 rpm. In some embodiments, the mixing in step iii) is carried out at about 400 rpm, about 600 rpm, about 800 rpm or about 1000 rpm. In some embodiments, the mixing is carried out at about 800 rpm.

In some embodiments, the mixing is carried out from about 1 min to about 2 hours, from about 2 min to about 1.5 hours, from about 5 min to about 60 min, from about 7 min to about 40 min, or from about 10 min to about 30 min. In some embodiments, the mixing is carried out for about 5 min, about 10 min, about 15 min, about 20 min, about 30 min, about 40 min, or about 60 min. In some embodiments, the mixing is carried out for about 20 min.

In some embodiments, the mixing in step iii) is followed by centrifugation and suspension of the resulting solids in a solution of a sugar alcohol to obtain the second suspension comprising the therapeutic particle. In some aspects of these embodiments, the solution of the sugar alcohol is an aqueous solution. In some aspects of these embodiments, the aqueous solution of sugar alcohol comprises from about 0.1 wt. % to about 25 wt. %, from about 0.5 wt. % to about 20 wt. %, from about 1 wt. % to about 15 wt. %, from about 2 wt. % to about 10 wt. %, or from about 3 wt. % to about 7 wt. % of mannitol. In some aspects of these embodiments, the aqueous solution of sugar alcohol comprises about 1 wt. %, about 2 wt. %, about 2.5 wt. %, about 3 wt. %, about 4 wt. %, about 4 wt. %, about 6 wt. %, or about 10 wt. %. In some aspects of these embodiments, the aqueous solution of sugar alcohol comprises about 2.5 wt. % of mannitol.

In some embodiments, the incorporation efficiency of the therapeutic protein in the particle is from about 75% to about 100%, from about 80% to about 100%, from about 85% to about 100%, from about 90% to about 100%, or from about 95% to about 100%. In some embodiments, the incorporation efficiency of the therapeutic protein in the particle is from about 90% to about 100%. In some embodiments, the incorporation efficiency of the therapeutic protein in the particle is about 85%, about 90%, about 92%, about 95%, about 99% or about 100%.

Methods of Using Particles of the Present Disclosure

The methods of the disclosure offer the ability to deliver a therapeutic protein to the desired biological target without exposing the therapeutic protein to the harsh physiological conditions (e.g., without exposing the therapeutic protein to the physiological condition of the stomach).

In some embodiments, the present disclosure provides a method of treating a disease or condition in a subject, comprising administering to the subject (e.g., the subject in need thereof) a therapeutically effective amount of the particle as described herein or the pharmaceutical composition comprising the particle as described herein. In some embodiments, the disease or condition is the disease of condition that is beneficially treated by the therapeutic protein in the particle.

In some embodiments, the therapeutic protein is a hormone useful in treating endocrine disorders (hormone deficiencies). (e.g., diabetes, diabetes mellitus, diabetic ketoacidosis, hyperkalaemia, hyperglycemia, growth failure due to GH deficiency or chronic renal insufficiency, Prader-Willi syndrome, Turner syndrome, AIDS wasting or cachexia with antiviral therapy, growth failure in children with GH gene deletion or severe primary IGF1 deficiency, postmenopausal osteoporosis, severe osteoporosis, or type 2 diabetes resistant to treatment with metformin and a sulphonylurea, or acromegaly).

In some embodiments, the therapeutic protein is useful in treating haemostasis and thrombosis (e.g., haemophilia A, haemophilia B, hereditary AT-III deficiency in connection with surgical or obstetrical procedures or for thromboembolism, venous thrombosis and purpura fulminans in patients with severe hereditary protein C deficiency, pulmonary embolism, myocardial infarction, acute ischaemic stroke, occlusion of central venous access devices, acute myocardial infarction, haemorrhage in patients with haemophilia A or B and inhibitors to factor VIII or factor IX, severe sepsis with a high risk of death, heparin-induced thrombocytopenia, blood-clotting risk in coronary angioplasty, acute evolving transmural myocardial infarction, deep vein thrombosis, arterial thrombosis, occlusion of arteriovenous cannula, or thrombolysis in patients with unstable angina).

In some embodiments, the therapeutic protein is an enzyme useful in treating metabolic enzyme deficiencies (e.g., Gaucher's disease, Pompe disease, glycogen storage disease type II, Hurler and Hurler-Scheie forms of mucopolysaccharidosis I, mucopolysaccharidosis II, Hunter syndrome, mucopolysaccharidosis VI, or Fabry disease). In some embodiments, the enzyme is useful in treating pulmonary and gastrointestinal-tract disorders (e.g., congenital α-1-antitrypsin deficiency, gas, bloating, cramps and diarrhea due to inability to digest lactose, cystic fibrosis, chronic pancreatitis, pancreatic insufficiency, post-Billroth II gastric bypass surgery, pancreatic duct obstruction, steatorrhea, poor digestion, gas, or bloating). In some embodiments, the enzyme is useful in treating immunodeficiencies (e.g., severe combined immunodeficiency disease due to adenosine deaminase deficiency or primary immunodeficiencies).

In some embodiments, the therapeutic protein is an antibody useful in treating cancer (e.g., bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, or testicular cancer; in particular sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osseocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma).

In some embodiments, the therapeutic protein is an antibody useful in treating an inflammatory disease or condition (e.g., rheumatoid arthritis, psoriasis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, or yersinial arthritis). In some embodiments, the therapeutic protein in useful in treating infectious disease (e.g., HIV infection).

In some embodiments, the disease or condition can be characterized by an insufficient amount of growth hormone, e.g., human growth hormone (hGH). For example, hGH can be used as a replacement therapy in children or adults with an hGH deficiency. The methods of the disclosure can also be used to deliver, e.g., human growth hormone to treat conditions which produce short stature but is not related to deficiencies in hGH, or in maintaining muscle mass to ameliorate muscle wasting as a result of diseases such as AIDS.

In some embodiments, the therapeutic protein is useful in treating haematopoiesis (e.g., anaemia, myelodysplasia, anaemia due to renal failure or chemotherapy, preoperative preparation, anaemia in patients with chronic renal insufficiency and chronic renal failure (+/− dialysis), neutropaenia, neutropaenia in AIDS or post-chemotherapy or bone marrow transplantation, severe chronic neutropaenia, leukopaenia, myeloid reconstitution post-bone-marrow transplantation, HIV/AIDS, or thrombocytopaenia (especially after myelosuppressive chemotherapy)).

In some embodiments, the therapeutic protein is useful in treating infertility. (e.g., assisted reproduction and treating infertility with luteinizing hormone deficiency). In some embodiments, the therapeutic protein is useful in immunoregulation.

In some embodiments, the therapeutic protein is useful in treating diseases or condition associated with growth regulation. (e.g., acromegaly, symptomatic relief of VIP-secreting adenoma and metastatic carcinoid tumours, spinal fusion surgery, bone injury repair, tibial fracture nonunion, lumbar, spinal fusion, precocious puberty, severe oral mucositis in patients undergoing chemotherapy or debridement adjunct for diabetic ulcers). In some embodiments, the therapeutic protein is useful in treating decubitus ulcer, varicose ulcer, debridement of eschar, dehiscent wound, sunburn, or acute decompensated congestive heart failure.

In some embodiments, the therapeutic protein is useful in enzymatic degradation of macromolecules. (e.g., many types of dystonia (e.g., cervical), debridement of chronic dermal ulcers and severely burned areas, cystic fibrosis, respiratory tract infections, respiratory tract infections in selected patients with FVC greater than 40% of predicted, debridement of necrotic tissue, or debridement of necrotic tissue or liquification of slough in acute and chronic lesions (e.g., pressure ulcers, varicose and diabetic ulcers, burns, postoperative wounds, pilonidal cyst wounds, carbuncles, and other wounds)). In some embodiments, the therapeutic protein is useful in organ transplantation (e.g. treating acute kidney transplant rejection). In some embodiments, the therapeutic protein is useful in treating pulmonary disorders (e.g., respiratory syncytial virus infection, asthma).

In some embodiments, the present disclosure provides particles useful for tissue regeneration or stem cell homing. In other embodiments, the particles and compositions comprising the particles as described herein are useful in tissue culturing (e.g. growth factor-loaded DSCS NPs can be used in various stem cell culture media to prolong the effects of the incorporated growth factors and reduce the cost of stem cell culture by eliminating frequent culture media replacement. For research purposes, protein free (unloaded) DSCS NPs can be used for protein pull-down enrichment, and analysis on SDS gels without separating the protein from the particles. In some embodiments, the particles and compositions described herein may be used for cosmetic purposes (e.g., unloaded DSCS NPs can be added to stem cells conditioned media to absorb growth factors secreted by the cells and used for special skin rejuvenation).

In some embodiments, the therapeutic particle comprising the therapeutic protein is useful in treating macular degeneration. In some embodiments, the therapeutic particle comprising the therapeutic protein is useful in treating pulmonary hypertension.

Compositions and Routes of Administration

The present application provides, inter alia, a composition comprising a particle (e.g., a therapeutic particle) as described herein. The composition can be a pharmaceutical composition in which the particle (e.g., a therapeutic particle) is included together with a pharmaceutically acceptable carrier.

The present application also provides pharmaceutical compositions comprising a particle comprising an effective amount of a therapeutic protein, and a pharmaceutically acceptable carrier. The compositions of the disclosure offer the ability to deliver a therapeutic protein that may be sensitive to organic solvents without exposure to the solvents which are needed in other preparations. Such compositions retain a high bioactivity of the therapeutic protein within the particle compared with the native form but with an enhanced stability. In some embodiments, the bioactivity of the therapeutic protein in the composition is in a range from about 70% to about 100%, from about 80% to about 100%, or from about 90% to about 100% of the bioactivity of a native therapeutic protein. In some embodiments, the bioactivity of the therapeutic protein in the composition is about 90%, about 95%, about 97%, or greater than 99% of the bioactivity of a native therapeutic protein. Thus, in some aspects there are provided compositions as described herein comprising a particle comprising a therapeutic protein, wherein the bioactivity of the therapeutic protein in the composition is in a range from about 70% to about 100%, from about 80% to about 100%, or from about 90% to about 100% of the bioactivity of a native therapeutic protein, or wherein the bioactivity of the therapeutic protein in the composition is about 90%, about 95%, about 97%, or greater than 99% of the bioactivity of a native therapeutic protein.

The controlled release profiles can afford enhanced pharmacokinetic profiles of a therapeutic protein within a subject, compared with a therapeutic protein in a subject that has not been loaded into a TNP. An enhanced pharmacokinetic profile can exhibit an improved property of one or more selected from AUC, half-life, clearance, mean residence time, and volume of distribution (Vss). In some embodiments, the AUC of a therapeutic protein in a composition of the disclosure is in a range from about 100% to about 1000%, from about 150% to about 700%, or from about 200% to about 500% of the AUC of a native therapeutic protein, or wherein the AUC of the therapeutic protein in the composition is about 150%, about 200%, about 250%, about 300%, about 350%, about 400%, about 450%, about 500%, or greater than 500% of the AUC of a native therapeutic protein. In some embodiments, the half-life of a therapeutic protein in a composition of the disclosure is in a range of from about 100% to about 100,000%, from about 100% to about 1000%, from about 100% to about 500%, from about 150% to about 400%, or from about 200% to about 300% of the half-life of a native therapeutic protein, or wherein the half-life of the therapeutic protein in the composition is about 150%, about 200%, about 250%, about 300%, or greater than 400% of the half-life of a native therapeutic protein. In some embodiments, the clearance of a therapeutic protein in a composition of the disclosure is in a range from about 1% to about 100%, from about 10% to about 90%, from about 20% to about 80%, from about 30% to about 70%, or from about 40% to about 80% of the clearance of a native therapeutic protein, or wherein the clearance of the therapeutic protein in the composition is about 3%, about 5%, about 10%, about 15%, about 20%, about 25%, about 30%, about 40%, about 50%, about 60%, about 70%, or about 80% of the clearance of a native therapeutic protein. In some embodiments, the mean residence time of a therapeutic protein in a composition of the disclosure is in a range from about 100% to about 1000%, from about 150% to about 700%, or from about 200% to about 500% of the mean residence time of a native therapeutic protein, or wherein the mean residence time of the therapeutic protein in the composition is about 150%, about 200%, about 250%, about 300%, about 350%, about 400%, about 450%, about 500%, or greater than 500% of the mean residence time of a native therapeutic protein.

As used herein, "substantially free of organic solvents" refers to compositions which are mostly or entirely free of organic solvents. For example, an aqueous mixture substantially free of organic solvents is an aqueous mixture which has been subjected to processes that have removed most or all organic solvents from the mixture. In some embodiments, a composition substantially free of organic solvents can comprise about 5% or less, about 2% or less, about 10% or less, about 0.5% or less, 0.10% or less 0.05% or less, or about 0.01% or less by weight of organic solvents. In some embodiments, a composition substantially free of organic solvents can comprise about 5%, about 2%, about 1%, 0.5%, about 0.1%, about 0.05%, or about 0.01% organic solvents. In some embodiments, a composition substantially free of organic solvents can comprise aqueous solutions comprising a pharmaceutically acceptable buffer. In some embodiments, a composition substantially free of organic solvents can comprise aqueous solutions comprising a pharmaceutically acceptable salt. Common pharmaceutically acceptable buffers include acetate (acetic acid and sodium acetate), citrate (citric acid and sodium citrate), and phosphate (sodium phosphate and disodium phosphate) buffers. Pharmaceutically acceptable salt solutions include dilute saline solutions. For example, the composition can be in a pH-buffered phosphate solution or a saline solution. In some embodiments, a composition substantially free of organic solvents is a composition in water. In some embodiments, a composition substantially free of organic solvents can be free of salts.

The carrier(s) are "acceptable" or "pharmaceutically acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the therapeutic proteins of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

The pharmaceutical compositions of the present application may be administered by an injection (e.g., subcutaneous, intramuscular or intravenous). For example, the pharmaceutical composition may be administered by injection into an eye of a subject, e.g., when the pharmaceutical composition comprises a protein useful in treating macular degeneration.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, a particle comprising a therapeutic protein is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031.

Topical administration of the pharmaceutical compositions of the present application is especially useful when the desired treatment involves areas or organs readily accessible by topical application.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form.

In some embodiments, the topical composition comprises a combination of a particle comprising a therapeutic protein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof).

In the pharmaceutical compositions of the present application, a particle comprising a therapeutic protein is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In some embodiments, an effective amount of a particle comprising a therapeutic protein can range, for example, from about 1 µg to about 1000 mg. In some aspects of these embodiments, the composition containing an effective amount of a particle comprising a therapeutic protein is administered once daily, twice daily, or thrice daily.

In some embodiments, an effective amount of a particle comprising a therapeutic protein can range, for example, from about 0.001 µg/kg to about 10 mg/kg.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Combination Therapy

One or more additional pharmaceutical agents or treatment methods such as, for example, anti-viral agents, chemotherapeutics, other anti-cancer agents, immune enhancers, anti-inflammatories, immunosuppressants, radiation, anti-tumor and anti-viral vaccines, cytokine therapy (e.g., IL2, GM-CSF, etc.), and/or tyrosine kinase inhibitors can be used in combination with the particle comprising a therapeutic protein, or a composition thereof as described herein. The agents can be combined with the present therapeutic particles in a single dosage form, or the agents can be administered simultaneously or sequentially as separate dosage forms. Any one of the therapeutic proteins described herein may be used as an additional agent to be used in combination with the particle and compositions of the present disclosure. In some embodiments, the additional agent is a stem cell (e.g., stem cell therapy).

Kits

The present invention also includes pharmaceutical kits useful, for example, in the treatment or prevention of any one of diseases or disorders referred to herein, which include one or more containers containing a pharmaceutical composition comprising a therapeutically effective amount of a particle of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Definitions

Unless defined otherwise, all technical and scientific terms used herein have the same meaning as is commonly understood by one of ordinary skill in the art to which this disclosure belongs.

As used herein, the singular forms "a," "an," and "the" include plural referents unless the context clearly dictates otherwise.

As used herein, the term "about" means "approximately" (e.g., plus or minus approximately 10% of the indicated value).

The term "particle" as used herein refers to a composition having a size from about 1 nm to about 1000 µm.

The term "nanoparticle" as used herein refers to a particle having a size (e.g., equivalent spherical diameter) from about 1 nm to about 1000 nm.

The term "particle size" (or "nanoparticle size" or "microparticle size") as used herein refers to the median size in a distribution of nanoparticles or microparticles. The median size is determined from the average linear dimension of individual nanoparticles, for example, the diameter of a spherical nanoparticle. Size may be determined by any number of methods in the art, including dynamic light scattering (DLS) and transmission electron microscopy (TEM) techniques.

The terms "Incorporation efficiency" and "Encapsulation efficiency" as used herein refer to the ratio of the amount of therapeutic protein that is incorporated into the particles (e.g., nanoparticles) to the initial amount of therapeutic protein used in preparation of the particle.

The terms "Loading capacity" and "loading efficiency" are used herein interchangeably and refer to the molar fraction of the therapeutic protein that is encapsulated to the molar fraction of the charged monosaccharide units of the particles (e.g., nanoparticles).

As used herein, the term "aqueous solvent" refer to a liquid comprising at least 50%, at least 60%, at least 70%, at least 90% or at least 95% of water. In some embodiments, aqueous solvent is water. In some embodiments, aqueous solvent is a buffer solution (e.g., Dulbecco's Phosphate-Buffered Saline (DPBS)).

As used herein, "room temperature" refers to ambient indoor temperature, typically a temperature from about 15° C. to about 25° C. In some embodiments, room temperature is 18° C.

EXAMPLES

Materials and Methods

Dextran sulfate sodium salt, weight-average MW 500 kDa, was purchased from Fisher Scientific. Chitosan (MW range 50-190 kDa, 75-85% deacetylated) (Catalog No. 448869), zinc sulfate, mannitol, Azure A chloride (Catalog No. 861049), and lysozyme (from chicken egg white), glutaric acid, malic acid, succinic acid, tartaric acid, 1-ethyl-3-(3-dimethylaminopropyl) carbodiimide (EDC), and N-hydroxysuccinimide (NHS) were obtained from Sigma-Aldrich. Cibacron brilliant red 3B-A (Catalog No. sc-214719) was purchased from Santa Cruz Biotechnology. Ultra Pure DNase/RNase-free distilled water was obtained from Invitrogen. Recombinant human SDF-1α and VEGF165 were prepared according to previously described protocols. (See, e.g., Lauten, E. et al. Nanoglycan complex formulation extends VEGF retention time in the lung. *Biomacromolecules* 2010, 11 (7), 1863-72; and Yin, T. et al. SDF-1 alpha in glycan nanoparticles exhibits full activity and reduces pulmonary hypertension in rats. *Biomacromolecules* 2013, 14 (11), 4009-20). Bovine serum albumin (BSA) was purchased from EMD Millipore. Basic fibroblast growth factor (FGF-2) and bone morphogenetic protein-2 (BMP-2) were purchased from Peprotech. SDF-1α ELISA kit (Human CXCL12/SDF-1α DuoSet) was purchased from R&D Systems.

Example 1—Preparation and Analysis of DSCS Nanoparticles

General Procedure for Nanoparticle Preparation:

DSCS nanoparticles were prepared in a total volume of 1.2-300 ml in this study. For a 300 ml preparation, 150 ml DS (1 mg/ml in $H_2O$) was stirred at 700 rpm and mixed with 37.5 ml CS (1 mg/ml, dissolved in 0.2% acetic acid/$H_2O$ and filtered consecutively through 0.8, 0.45, and 0.2 µm SFCA membranes) for 15 min. The stirring speed was then increased to 800 rpm, and 5.8 ml 200 mM $ZnSO_4$ was added at 1 ml/min through a syringe pump. The mixture was stirred for another 60 min before the addition of 100 ml of 15% solution of mannitol. The DSCS nanoparticles were precipitated by centrifugation at 20,000×g for 20 min. The particle pellets were washed twice with 70 ml water and centrifuged at 30,000×g for 40 min. The final particles were suspended in 12 ml of 5% solution of mannitol, divided into 0.5 ml aliquots, frozen at −80° C., and lyophilized for 3 days. The dried particles were stored desiccated at 4° C. until use.

Particle Size and Zeta Potential Optimization Studies

A DelsaNano C Particle Analyzer (Beckman) was used for the particle analysis following procedures described previously (See, e.g., Bader et al, Preparation and characterization of SDF-1 alpha-chitosan-dextran sulfate nanoparticles. *J Vis Exp* 2015, (95), 52323). Briefly, 10-15 µl particle samples were diluted in 0.5 ml or 2.5 ml water for size or zeta potential measurement, respectively. Standard operating procedures of the instrument were followed. Autocorrelation functions were analyzed by the Contin algorithm, and particle diameters were presented as cumulants. Zeta potentials were calculated from electrophoretic mobility using Smoluchowski approximation.

Effect of Mannitol Concentration:

The effect of mannitol on the stability of DSCS nanoparticles during lyophilization is shown in FIG. 1. In the presence of 0.3-5% mannitol, both the size and polydispersity index of the particles were gradually decreased. The concentration effect plateaued at 2.5-5%, and 5% mannitol was chosen for the DSCS nanoparticle preparation.

Figure 2:
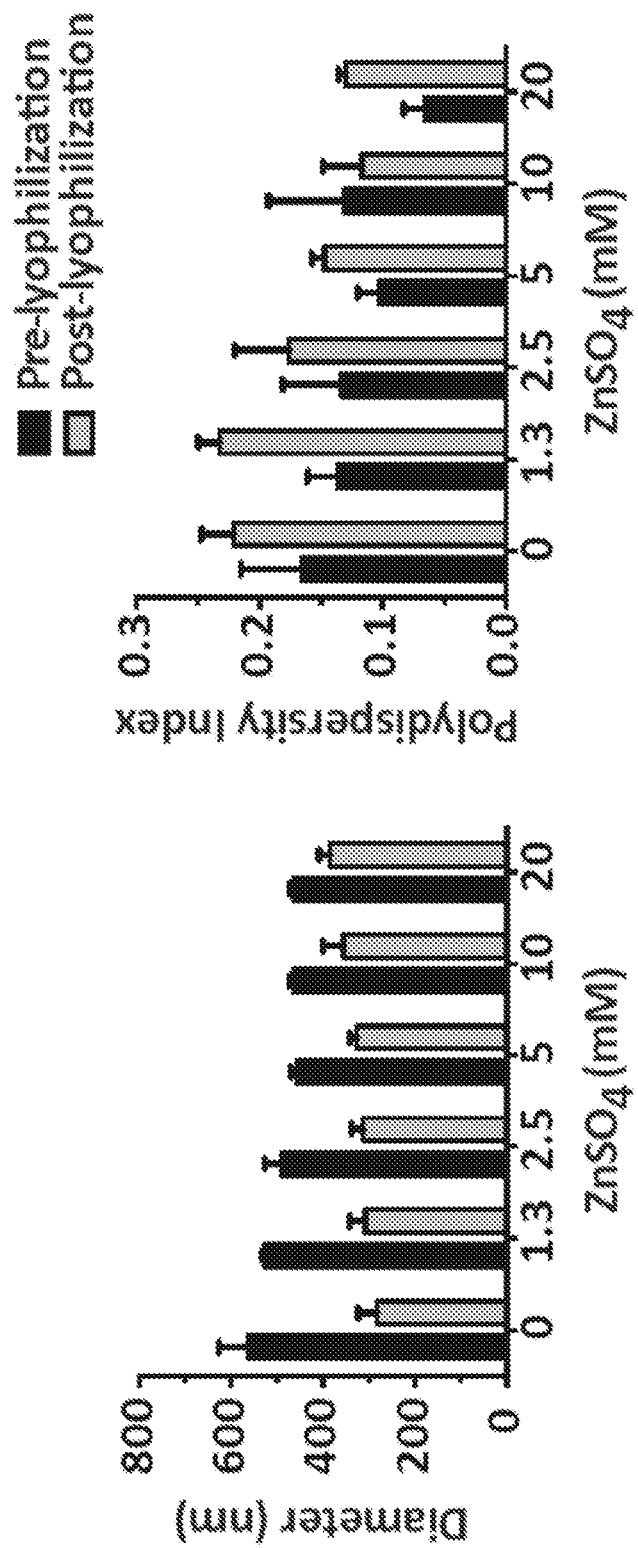
FIG. 2 is a bar graph showing effect of zinc concentrations on DSCS particle size. Particles were prepared with the indicated concentrations of $ZnSO_4$, and resuspended in 5% mannitol after preparation. Particle sizes were measured before (black bar) and after lyophilization (gray bar). Data represent the mean±SD of measurements of three separate preparations.

Effect of Zinc Concentration:

The effect of zinc concentration on particle size is shown in FIG. 2. Increasing zinc concentration from 0 to 20 mM led to a particle size decrease prior to lyophilization but increase after lyophilization. In both cases the polydispersity indices of the particles were decreased with increasing zinc concentrations. A zinc sulfate concentration of 6 mM was chosen for the DSCS nanoparticle preparation.

Effect of Lyophilization:

Lyophilization reduced the overall size of the particles; however, the polydispersity indices of the particles were increased (See FIG. 2). The increase in polydispersity reflected an increase in heterogeneity of the particles resulting from the generation of ultra-fine particles during the lyophilization process. To ultrafine particles from the rest of the particles, centrifugation (21,000×g for 20 min) was carried out after reconstitution of lyophilized DSCS nanoparticles and the resulting supernatant was discarded. The parameters of the finally formulated particles are shown in Table 1:

TABLE 1

Size and charge properties of large-scale nanoparticle preparation

| Nanoparticle Preparation phase | Diameter (nm) | Polydispersity Index | Zeta Potential (mV) |
|---|---|---|---|
| Pre-lyophilization | 455 ± 14 | 0.11 ± 0.2 | −45.9 ± 5.4 |
| Post-lyophilization | 349 ± 15 | 0.14 ± 0.04 | −40.0 ± 2.6 |
| Post-centrifugation | 377 ± 10 | 0.11 ± 0.01 | −43.1 ± 1.5 |

Quantification of Un-Neutralized DS in DSCS Nanoparticles (Azure A Assay)

To determine the amount of charged DS in DSCS NPs, an Azure A metachromatic assay was used. Azure A assay has been previously established to measure concentrations of dextran sulfate (See, e.g., Ellis, H. et al. The estimation and recovery of dextran sulphates in biological fluids. J. Clin. Pathol. 1959, 12, 467-72) and heparin (See, e.g., Grant, A. et al. Metachromatic activity of heparin and heparin fragments. *Anal. Biochem.* 1984, 137 (1), 25-32) in solutions.

Azure A was dissolved in water at 1 mg/ml as stock solution (stored at 4° C.), and diluted to 0.02 mg/ml in water as working solution. For spectrophotometric analysis, 2 ml Azure A working solution was added to a polystyrene cuvette and mixed with 20 µl DS solution. Measurements were made within 15 min of mixing. To determine DS concentration in a 96-well plate format, 10 µl DS standards (made with dextran sulfate sodium salt) or NP samples in a concentration range of 0-0.20 mg/ml were added to plate wells. The Azure A working solution (200 µl) was added next, followed by mixing on a plate shaker for 2 min. Absorbance was read at a wavelength of 620 nm. Samples were run in triplicate, and empty wells were used as the instrument blank.

Figure 3A:
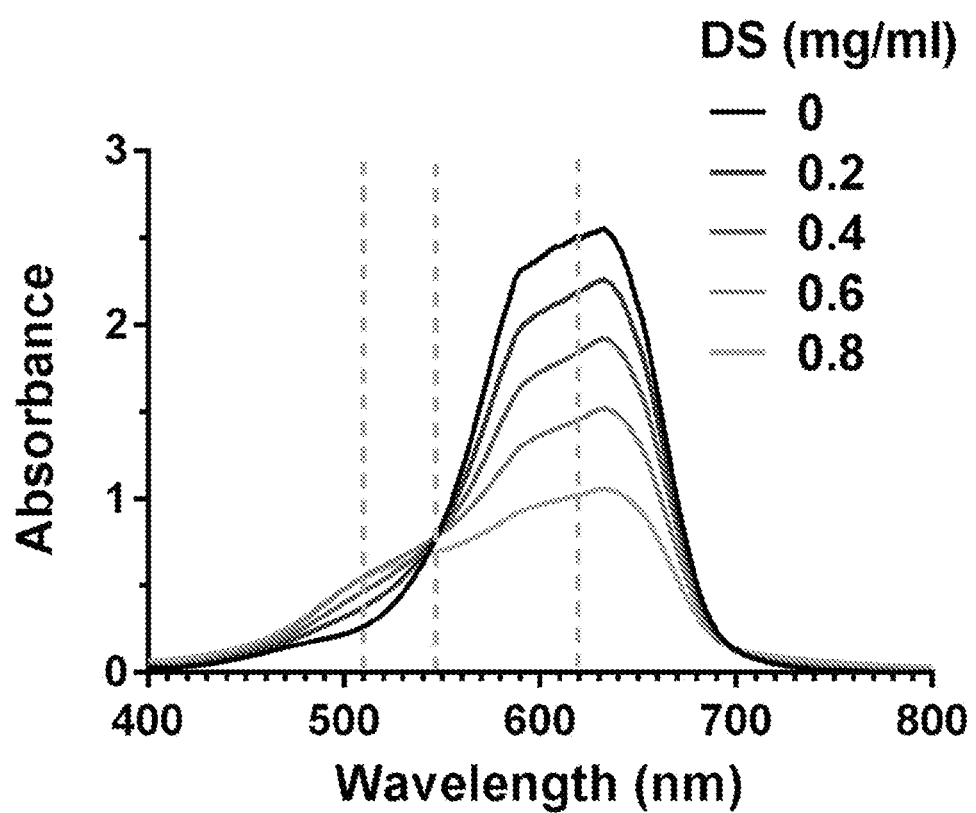
FIG. 3A is a line graph showing absorption spectra of Azure A. The dotted lines mark the wavelengths at which the absorbance proportionally changed (510 and 620 nm) or did not change (548 nm, isosbestic point) with increasing DS concentration.
Figure 3B:
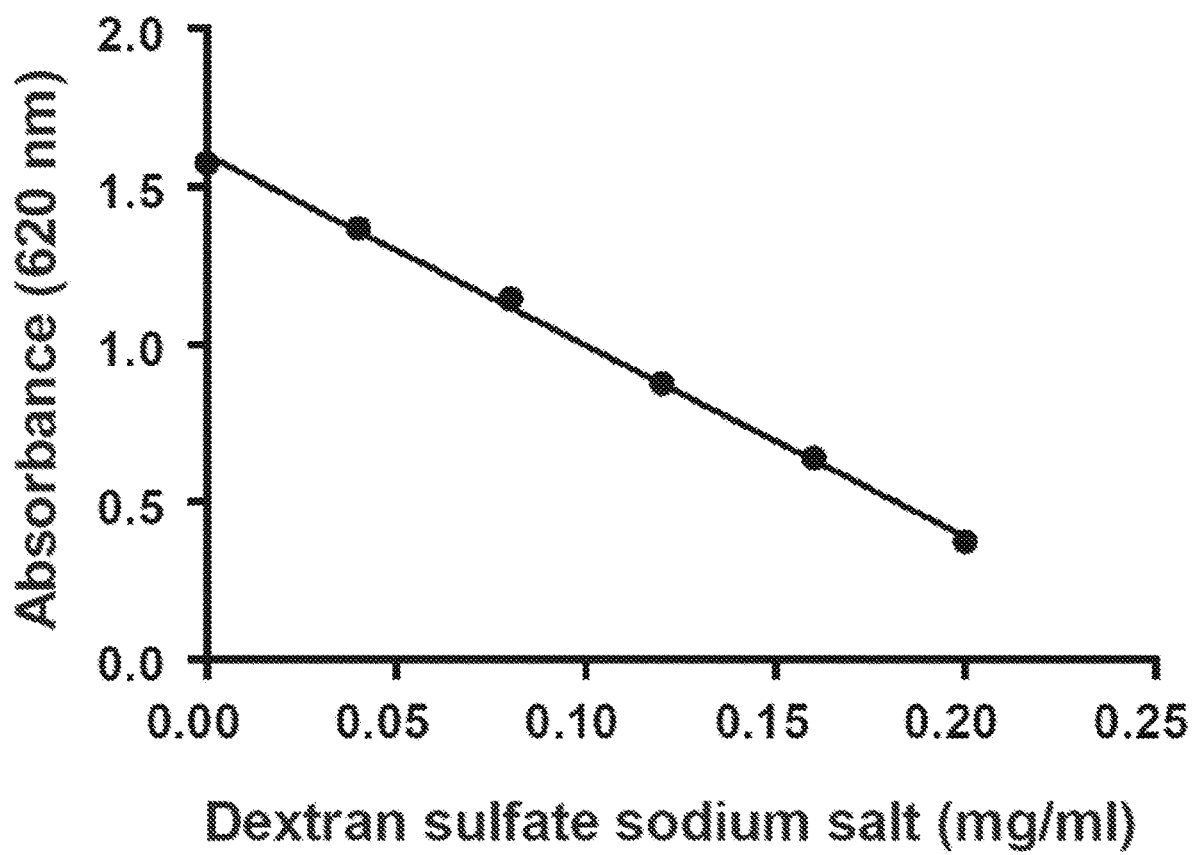
FIG. 3B is a line graph showing an example of a standard curve used for measuring charged DS in a 96-well plate format.

The absorption spectra of Azure A after interacting with DS solutions is shown in FIG. 3A. A typical standard curve is shown in FIG. 3B, and the standard solutions were made with dextran sulfate sodium salt at concentrations from 0.04-0.2 mg/mL.

To confirm that Azure A assay detects charged DS in DSCS NPs, the assay was carried out to measure DS concentration in each step of the particle preparation. The results are shown in Table 2:

TABLE 2

Amount of azure A-detectable dextran sulfate (DS) at various steps during the preparation of DSCS nanoparticle[1].

| Preparation Steps | Volume (mL) | DS conc. (mg/mL) | Total DS (mg) | % Input DS |
|---|---|---|---|---|
| Initial DS | 150 | 0.99 | 148.5 | 99.0 |
| Post CS addition | 187.5 | 0.64 | 120 | 80.0 |
| Post ZnSO4 add.[2] | 193.3 | 0.63 | 121.8 | 81.2 |
| Post mannitol add. | 293.3 | 0.41 | 120.3 | 80.2 |
| 1st spin pel. susp.[3] | 72 | 0.16 | 11.5 | 7.7 |
| 2nd spin pel. susp. | 72 | 0.12 | 8.6 | 5.7 |
| Final pel. susp. | 12 | 0.55 | 6.6 | 4.4 |

[1]DSCS nanoparticles were prepared according to the procedure described in the general procedure. After each preparation step, 0.1 ml aliquot was removed and diluted in water for Azure A measurement.
[2]add., addition.
[3]pel. susp., pellet suspension. Data represent the mean from four separate preparations.

Measurement of Reduction in DS Content:

As can be seen from the data presented in Table 2, the total detectable amount of DS was reduced by ~20% after addition of 37.5 ml of 1 mg/ml CS to 150 ml of 1 mg/ml DS in the first step of the NP preparation, resulting from neutralization of sulfate groups in DS by CS. Calculation of un-neutralized DS content in DSCS nanoparticles was performed as follows: The mass of a glucose sulfate unit in DS (sulfur content 17%) is approximately 397, assuming a glucose unit (mass=180) with 2.3 sodium sulfate substitutions [(23+97-18)*2.3=235] and one glycosidic bond (ignoring 5% branching) (−18); and the mass of a glucosamine unit in CS (80% deacetylated) is 169, assuming 0.8 glucosamine unit (179*0.8=143), 0.2N-acetylglucosamine unit (221*0.2=44), and one glycosidic bond (−18). At the weight ratio of DS to CS of 4:1, the ratio of saccharide units in DS and CS is 1:0.59. Each unit has on average 2.3 negative charges in DS and 0.8 positive charges in CS. Thus, the total charge ratio between DS and CS is ~2.3:0.47 (5:1). When neutralized, charged DS would comprise ~80% of total. This change remained after zinc sulfate and mannitol addition, indicating that the particle structure itself did not affect the detectability of its charged DS by Azure A.

Measurement of CS Content:

Cibacron brilliant red 3B-A colorimetric assay (See, e.g., Mendelovits, A et al, Improved colorimetric determination of chitosan concentrations by dye binding. *Appl Spectrosc* 2012, 66 (8), 979-82; and Muzzarelli, R. A., Colorimetric determination of chitosan. *Anal. Biochem.* 1998, 260 (2), 255-7) was used to measure the concentration of free CS. Using the assay, chitosan was not detected in the mixture of DS and CS, indicating complete neutralization of CS.

Example 2—Incorporation of Proteins into DSCS Nanoparticles

General Procedure for Incorporation of Proteins into Nanoparticles:

Prior to the protein incorporation, aliquots of lyophilized DSCS nanoparticles were reconstituted with water (e.g., 0.5 ml) and centrifuged at 21,000×g for 20 min to remove ultra-fine particles. The pellets were resuspended in 0.5 ml 2.5% mannitol, and the Azure A assay was performed to determine the concentration of charged DS in the suspended NPs. The protein incorporation was then carried out as follows:

a) The amount of nanoparticles containing 40 μg charged DS was transferred to a 2 ml glass vial and mixed with water or otherwise specified buffer solutions to a total volume of 0.3 ml. The nanoparticles were then stirred at 800 rpm, and 0.1 ml protein solution was added slowly. The stirring speed was reduced to 300 rpm and continued for 20 min to complete the incorporation reaction or b) Incorporation reactions were carried out by diluting specified amounts of DSCS NP and protein in water, 50% PBS, or otherwise noted buffer solutions, and adding protein solution slowly to NPs while stirring at 800 rpm. Total reaction volume was 0.3 ml or in some cases 0.15 ml which were placed in a 2 ml glass vial with a 1.5×8 mm stir bar, or a 1.5 ml tube with a 3×3 mm stir bar respectively. The mixture was stirred at 300 rpm for another 20 min.

General Protocol for Analysis of Protein Incorporation Efficiency

After the incorporation reactions, particles were separated from unincorporated protein by centrifugation at 21,000×g for 20 min. Supernatants were collected and pellets were resuspended in 2.5% mannitol to the original volume. Equal volumes of supernatants and pellets were loaded on a 4-20% SDS gel for electrophoresis. The gels were stained with Coomassie blue and protein bands were quantified by densitometric analysis as previously described using BioRad ImageLab software. (See, e.g., Bader, A. et al, Preparation and characterization of SDF-1 alpha-chitosan-dextran sulfate nanoparticles. *J Vis Exp* 2015, (95), 52323).

SDF-1α

SDF-1α is a chemokine and an important stem cell homing factor (See, e.g., Stebler, J et al. Primordial germ cell migration in the chick and mouse embryo: the role of the chemokine SDF-1/CXCL12. *Dev. Biol.* 2004, 272, (2), 351-61; Sharma M. et al. Stromal-derived factor-1/CXCR4 signaling: indispensable role in homing and engraftment of hematopoietic stem cells in bone marrow. *Stem Cells Dev* 2011, 20, (6), 933-46; and Ghadge S. et al. SDF-1αlpha as a therapeutic stem cell homing factor in myocardial infarction. *Pharmacol. Ther.* 2011, 129, (1) 97-108). Its mature form has a molecular weight of 7,963 Da and isoelectric point 9.9. SDF-1α is a monomer in solutions but forms a dimer upon binding to heparin (See, e.g., Fermas S. et al. Sulfated oligosaccharides (heparin and fucoidan) binding and dimerization of stromal cell-derived factor-1 (SDF-1/CXCL 12) are coupled as evidenced by affinity CE-MS analysis. *Glycobiology* 2008, 18, (12), 1054-64; and Sadir R et al. Characterization of the stromal cell-derived factor-1 alpha-heparin complex. *J. Biol. Chem.* 2001, 276, (11), 8288-96). Alkaline pH also promotes dimer formation of SDF-1α. SDF-1α has a specific heparin-binding site which occupies 12-14 sugar units in a heparin fragment (See, e.g., Veldkamp C. et al. The monomer-dimer equilibrium of stromal cell-derived factor-1 (CXCL12) is altered by pH, phosphate, sulfate, and heparin. *Protein Sci.* 2005, 14, (4), 1071-81; and Amara A et al. Stromal cell-derived factor-1 alpha associates with heparan sulfates through the first beta-strand of the chemokine. *J. Biol. Chem.* 1999, 274, (34), 23916-25).

Formation and Characterization of SDFNPs:

To determine the stoichiometric ratio between SDF-1α and charged DS in DSCS NP in the incorporation study, the numbers of sugar units in charged DS were calculated, using the mass of a glucose sulfate unit in DS of 379 (see above description). The incorporation reaction was carried out by mixing SDF-1α with DSCS NPs at various ratios, followed by a centrifugation to separate un-incorporated SDF-1α from DSCS NPs. The amount of SDF-1α in pellet and supernatant fractions was analyzed on SDS gels. The result of incorporation of SDF-1α into pre-formed DSCS nanoparticles is shown in FIG. 4A and FIG. 4B.

Figure 4A:
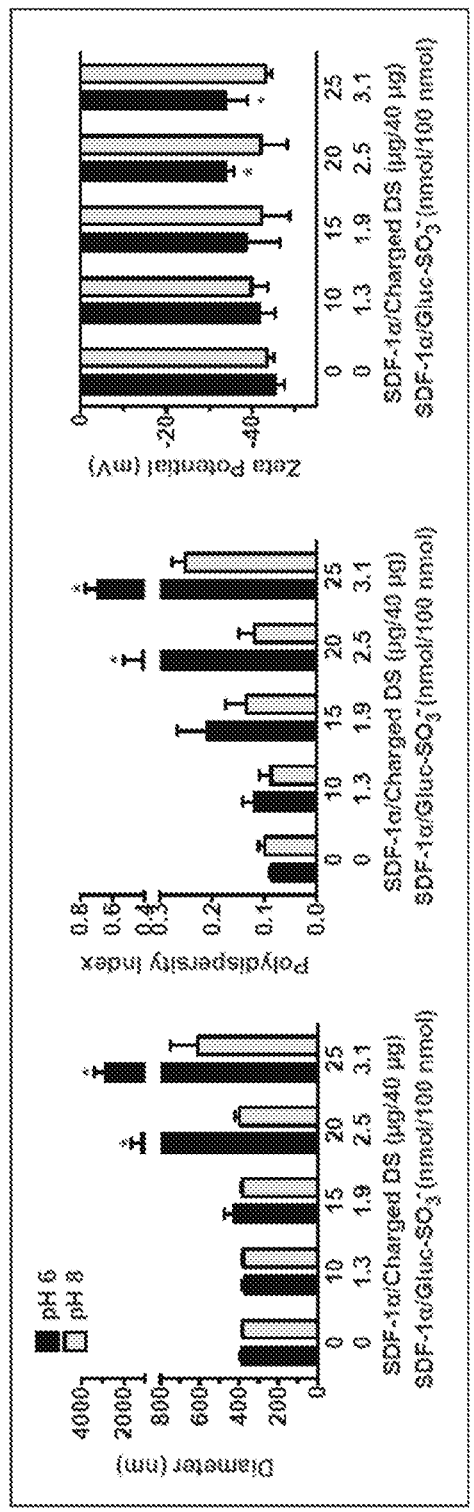
FIG. 4A shows particle sizes and zeta potentials of the SDF-1α-incorporated particles. Black bars indicate reactions were carried out in water at pH 6, and gray bars in 30 mM Tris-HCl at pH 8. SDF-1α and DSCS nanoparticles were mixed at the indicated ratios, which are expressed as either number of μg SDF-1α per 40 μg charged DS, or number of nmol SDF-1α per 100 nmol charged glucose sulfate units (Gluc-SO$^{3-}$) in DSCS nanoparticles.

FIG. 4A shows that for reactions carried out in water (pH 6), the particle size and zeta potential were not significantly altered at SDF-1α ratios between 1.3-1.9 nmol per 100 nmol charged glucose sulfate units in DSCS NPs. Beyond this point, the particles were markedly aggregated. Alkaline pH (pH 8) allowed some more SDF-1α loading (up to 2.5 nmol per 100 nmol charged glucose sulfate units in DSCS NPs) before inducing aggregation. The aforementioned loading limit of DSCS NP (in average ~1.5 nmol SDF-1α/100 nmol charged glucose sulfate units in DSCS NP) suggests that less than 10% of total charged DS can be occupied before affecting NP stability.

Figure 4B:
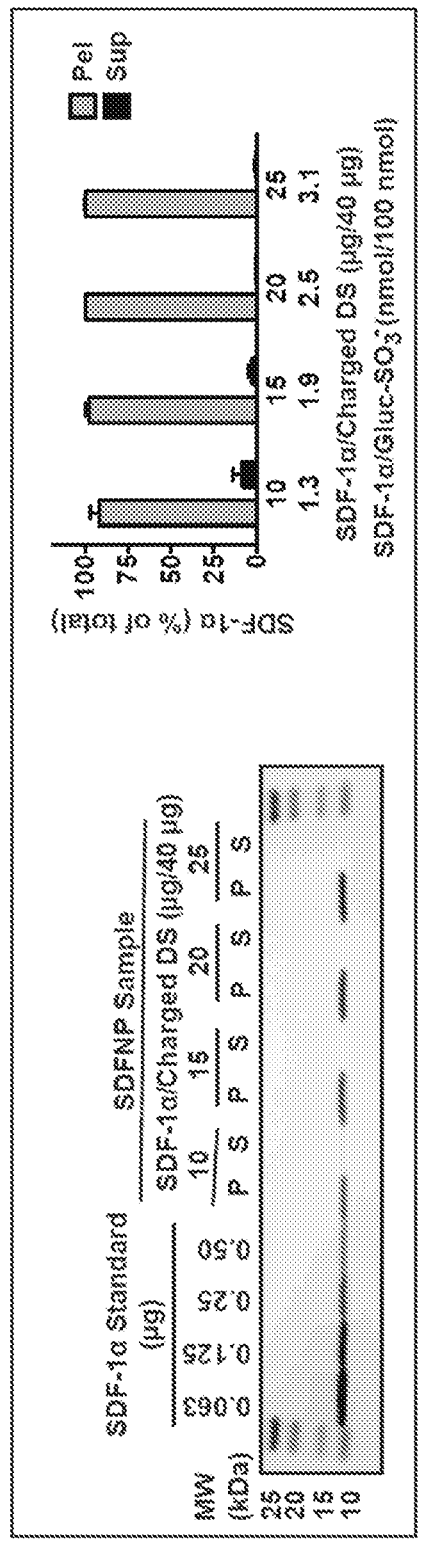
FIG. 4B shows (left panel) SDS gel analysis of the incorporation after centrifugation to separate the particles (pellet, P) from unincorporated protein (supernatant, S) and (right panel) densitometric quantification of SDF-1α contents in the gel bands, wherein graphs represent mean±SD from three separate preparations, *p<0.05 compared to no SDF-1α control.

FIG. 4B shows that the incorporation efficiency was 92-100% at all of the SDF-1α loading amounts tested (1-3 nmol/100 nmol charged saccharide units), indicating that the charged DS in DSCS nanoparticles was capable of binding more SDF-1α, although the extra binding caused aggregation of the particles. This incorporation efficiency was greater than that obtained previously using an entrapment method, and the resulting particle size was smaller than previously obtained (See, e.g., Yin, T. et al, SDF-1 alpha in glycan nanoparticles exhibits full activity and reduces pulmonary hypertension in rats. *Biomacromolecules* 2013, 14 (11), 4009-20, wherein the incorporation efficiency was 66-80% and particle size was ~640 nm).

VEGF

VEGF is an important growth factor involved in angiogenesis and vasculogenesis. (See, e.g., Ferrara, N., Molecular and biological properties of vascular endothelial growth factor. *J Mol Med* (Berl) 1999, 77, (7), 527-43). The protein is a disulfide-linked homodimer with MW of ~40,000 Da (each monomer without glycosylation is 19,166 Da) and an isoelectric point of 7.6. VEGF binds to heparin via two heparin-binding domains located at the carboxyl-terminus of each monomer. (See, e.g., Fairbrother, W et al. Solution structure of the heparin-binding domain of vascular endothelial growth factor. *Structure* 1998, 6, (5), 637-48). The binding domain in each monomer occupies 6-7 sugar units and homodimer VEGF requires 14 sugar units for tight binding. (See, e.g., Robinson, C. et al. VEGF165-binding sites within heparin sulfate encompass two highly sulfated domains and can be liberated by K5 lyase. *J. Biol. Chem.* 2006, 281, (3), 1731-40; and Zhao, W et al. Binding affinities of vascular endothelial growth factor (VEGF) for heparin-derived oligosaccharides. *Biosci Rep* 2012, 32, (1), 71-81).

Figure 5A:
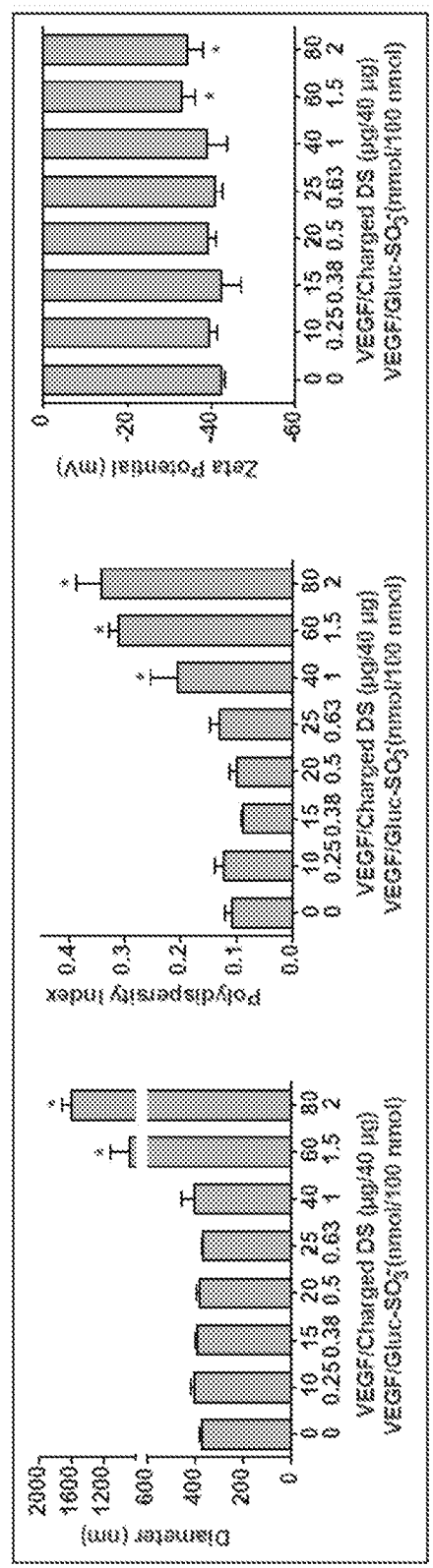
FIG. 5A shows particle sizes and zeta potentials of resulting VEGF-incorporated particles. VEGF and DSCS nanoparticles were mixed at the indicated ratios, which were achieved through increasing the amount of VEGF and keeping the fixed amount of DSCS nanoparticles at the lower ratios (10-25 μg VEGF/40 μg DS) or vice versa at higher VEGF/NP ratios (20-80 μg/40 μg DS).
Figure 5B:
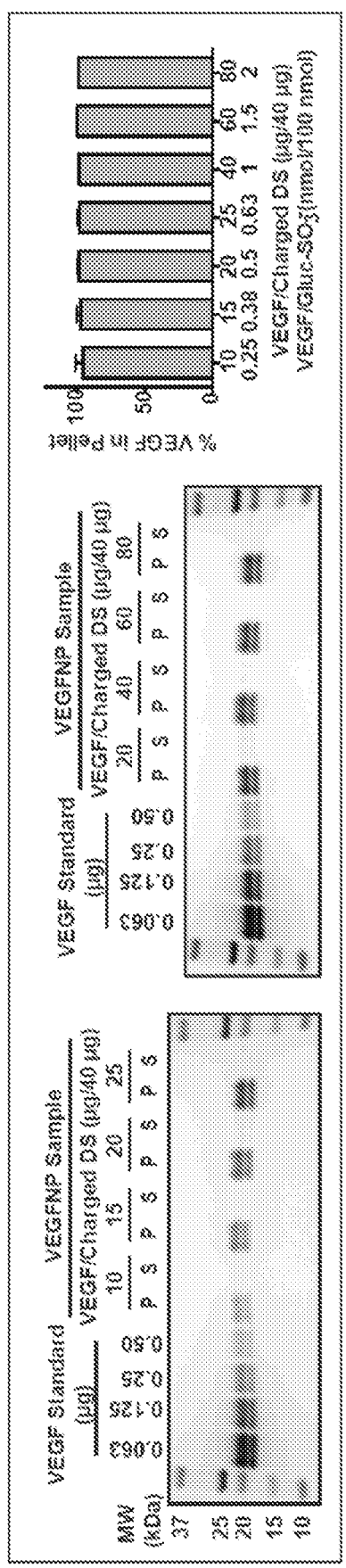
FIG. 5B shows SDS gel analysis of VEGF incorporation (left and middle panels) and the incorporation efficiency obtained from densitometric analyses of the gel bands (right panel). Data represent the mean±SD from three separate preparations. VEGF and DSCS nanoparticles were mixed at the indicated ratios, which were achieved through increasing the amount of VEGF and keeping the fixed amount of DSCS nanoparticles at the lower ratios (10-25 μg VEGF/40 μg DS) or vice versa at higher VEGF/NP ratios (20-80 μg/40 μg DS).

Formation and Characterization of VEGF NPs:

Incorporation of VEGF into pre-formed DSCS nanoparticles is shown in FIG. 5. The data in FIG. 5 show that the maximal loading of VEGF without significantly affecting the size and zeta potential of the particles was 0.63-1 nmol VEGF per 100 nmol charged glucose sulfate units in DSCS NPs, and the incorporation efficiency was 96-100% at the tested VEGF loading amounts (up to 2 nmol). These results are similar to that obtained from SDF-1α incorporation, i.e., out of 100 nmol charged sugar units in DSCS NPs, only 14 nmol could be occupied without affecting the stability of the particles, although the particles were capable of binding more of the protein. Similar to that found with SDF-1α, the loading limit of VEGF suggested that less than 10% charged glucose sulfate unit DSCS NP can be occupied without affecting the stability of the NPs.

The incorporation efficiency was 96-100% at all tested VEGF loading amounts (0.25-2 nmol/100 nmol charged saccharide units) and was greater than that achieved by an entrapment method. (For example, Lauten, E. et al. Nanoglycan complex formulation extends VEGF retention time in the lung. *Biomacromolecules* 2010, 11, (7), 1863-72 showed incorporation efficiency of ~40%; and Huang, M et al. Polyelectrolyte complexes stabilize and controllably release vascular endothelial growth factor. *Biomacromolecules* 2007, 8, (5), 1607-14 showed 50-80% incorporation efficiency).

Comparison Between Incorporation of SDF-1α, VEGF and BSA into Pre-Made DSCS Nanoparticles Albumin and globulins are the most abundant proteins in blood. As proteins can adsorb to the surfaces of various inorganic/organic materials, the adsorption of these proteins to pre-formed DSCS NPs was examined.

Figure 6:
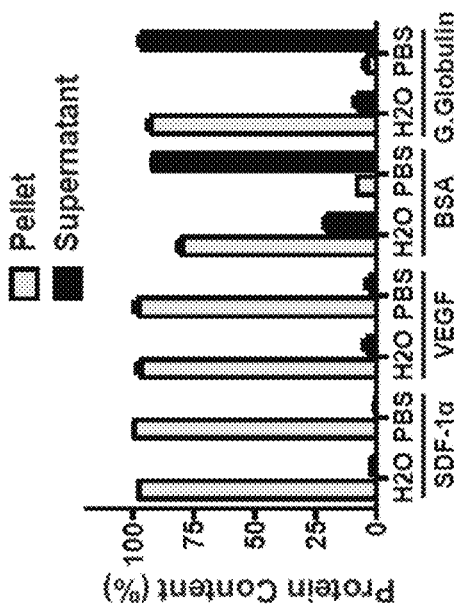
FIG. 6 shows protein contents in the pellet (P) and supernatant (S) fractions analyzed by SDS gel electrophoresis (Left), followed by densitometric analysis of the protein distribution based on analysis of the bands (right). Data represent the mean±SD from three separate incorporation reactions. Incorporations were carried out by mixing proteins (20 μg SDF-1α or VEGF or 50 μg BSA) with DSCS nanoparticles (containing 40 μg charged DS) in water ($H_2O$) or 50% PBS (PBS) for 20 min. Particles were then separated from unincorporated proteins by centrifugation.
Figure 6:
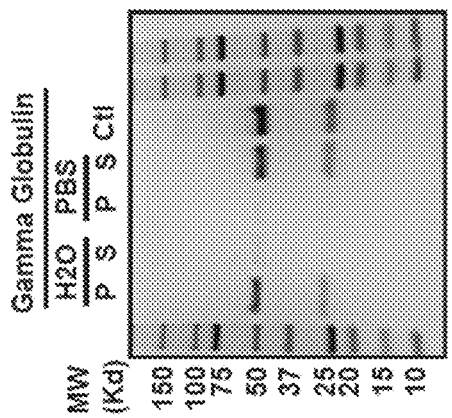
Figure 6:
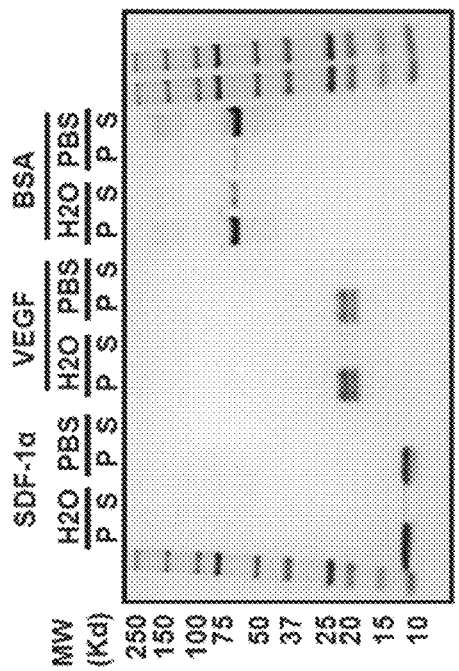

BSA is the most abundant protein in serum; it binds and transports various small or macromolecules in blood. BSA has a MW of 66,463 Da, an isoelectric point of 4.7-5.6, and no heparin-binding site or domain in its sequence. Incorporation of BSA to DSCS nanoparticles was initially tested in water and was found to be rather efficient:

a) as shown in FIG. 6, mixing 50 μg BSA (0.75 nmol) with 40 μg charged DS in DSCS nanoparticles resulted in 80% incorporation of BSA into the NPs. Nevertheless, in the presence of 50% Dulbecco's Phosphate-Buffered Saline (PBS), only 8% of BSA was incorporated; or b) 50 μg of bovine serum albumin (BSA) (0.75 nmol) or goat gamma globulin (0.42 nmol) were mixed with DSCS NPs (containing 100 nmol charged glucose sulfate units) in water or 50% phosphate buffered saline (PBS). Significant amounts of BSA and gamma globulin were adsorbed to DSCS NPs when mixed in water (80% and 92%, respectively), while only 8% and 4% adsorbed, respectively, when mixed in 50% PBS.

In contrast, incorporations of SDF-1α and VEGF to DSCS NPs were not affected by 50% PBS (See FIG. 6).

Incorporation of Lysozyme, FGF-2, and BMP-2 into Pre-Made DSCS Nanoparticles

Incorporation of lysozyme, FGF-2, and BMP-2 were studied in 50% PBS.

Lysozyme (MW 14.3 kDa, pI 11.4) is not a heparin-binding protein (See, e.g., Ori, A et al. A systems biology approach for the investigation of the heparin/heparan sulfate interactome. *J. Biol. Chem.* 2011, 286, (22), 19892-904), but has been previously shown to bind heparin in low salt solutions. (See, e.g., Zou, S et al. Heparin-binding properties of lactoferrin and lysozyme. *Comp Biochem Physiol* B 1992, 103, (4), 889-95; and Van de Weert, M et al. Complex coacervation of lysozyme and heparin: complex characterization and protein stability. *Pharm Res* 2004, 21, (12), 2354-9). Purified lysozyme could be obtained from commercial sources in relatively large quantity and low cost.

FGF-2 (MW 17.1 kDa, pI 9.6) is a monomeric protein and forms a dimer upon binding to heparin. (See, e.g., DiGabriele, A. et al. Structure of a heparin-linked biologically active dimer of fibroblast growth factor. *Nature* 1998, 393, (6687), 812-7; Faham, S. et al. Heparin structure and interactions with basic fibroblast growth factor. *Science* 1996, 271, (5252), 1116-20; and Schlessinger, J. et al. Crystal structure of a ternary FGF-FGFR-heparin complex reveals a dual role for heparin in FGFR binding and dimerization. *Mol. Cell* 2000, 6, (3), 743-50).

BMP-2 (MW 25.8 kDa, pI 8.2) is a disulfide-linked homodimeric heparin-binding protein. (See, e.g., Ruppert, R. et. al. Human bone morphogenetic protein 2 contains a heparin-binding site which modifies its biological activity. *Eur. J. Biochem.* 1996, 237, (1), 295-302; and Vallejo, L et al. Folding and dimerization kinetics of bone morphogenetic protein-2, a member of the transforming growth factor-beta family. *FEBS J.* 2013, 280, (1), 83-92).

Figure 7:
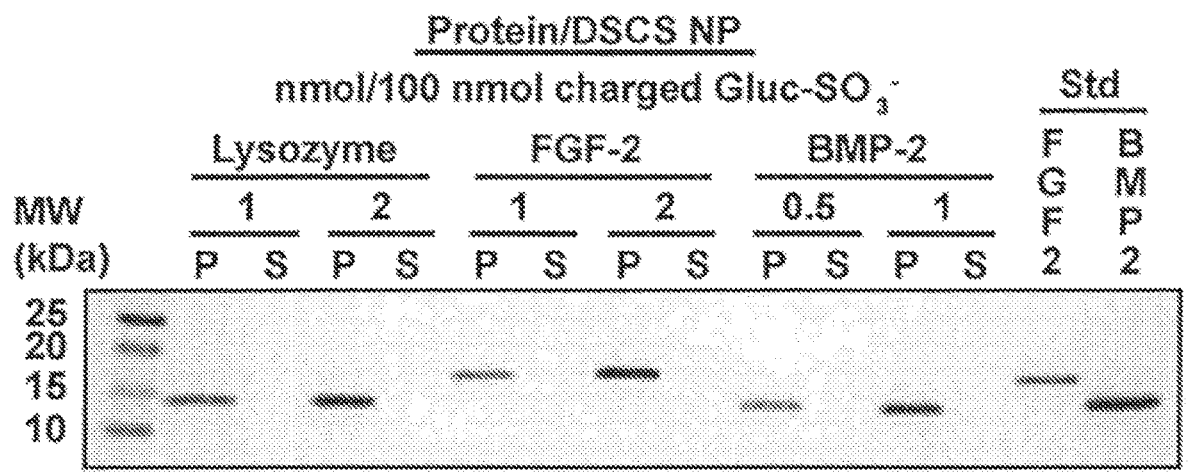
FIG. 7 shows equal volumes of pellet (P) and supernatant (S) fractions loaded to SDS gel for estimation of the incorporation efficiency. Data are from one incorporation experiment. Incorporation reactions were carried out in 50% PBS at the indicated molar ratios of protein and charged sugar units (Gluc-SO$^{3-}$) in DSCS nanoparticles. Particles were immediately spun down after the reactions, and resuspended in 2.5% mannitol to the original volume.

Incorporation of each of the proteins was examined at two different loading ratios. For lysozyme and FGF-2, the ratios were 1 or 2 nmol protein per 100 nmol charged sugar units in DSCS NPs; for BMP-2, the ratios were reduced to half, as BMP-2 is a dimer. As shown in FIG. 7 and Table 3, incorporation efficiencies of these proteins in 50% PBS were between 95-100%. Size and zeta potential of DSCS NPs were not significantly changed except for that of FGF-2-incorporated DSCS NPs at a protein-to-charged glucose sulfate unit ratio 2:100. Together with the findings from SDF-1α and VEGF incorporation, the maximum loading of heparin-binding proteins to DSCS NPs was approximately 1.5 nmol for monomeric proteins or 0.75 nmol for dimeric proteins per 100 nmol charged glucose sulfate units in DSCS NP No significant aggregation was found in these samples. The polydispersity indices were increased in the 2 nmol FGF-2 and 1 nmol BMP-2 samples, suggesting that they were approaching their loading limits.

TABLE 3

Incorporation of proteins into pre-formed DSCS NPs[1]

| Protein | Protein:GlucSO$_3^-$ (nmol:nmol) | Incorp. Efficiency (%) | Diameter (nm) | Polydisp. Index | Zeta Potential (mV) |
| --- | --- | --- | --- | --- | --- |
| None | | | 336 ± 4 | 0.08 ± 0.01 | −40.6 ± 1.6 |
| FGF-2 | 1:100 | 95 ± 1 | 356 ± 11 | 0.10 ± 0.03 | −41.9 ± 3.1 |
| FGF-2 | 2:100 | 96 ± 1 | 437 ± 75 | 0.22 ± 0.06 | −43.3 ± 2.9 |
| BMP-2 | 0.5:100 | 100 | 380 ± 6 | 0.11 ± 0.02 | −42.6 ± 3.2 |
| BMP-2 | 1:100 | 100 | 389 ± 11 | 0.09 ± 0.03 | −41.7 ± 0.2 |
| Lysozyme | 1:100 | 100 | 357 ± 1 | 0.09 ± 0.01 | −43.5 ± 3.5 |
| Lysozyme | 2:100 | 100 | 353 ± 5 | 0.09 ± 0.02 | −44.4 ± 3.8 |

[1]Incorporation reactions were carried by mixing indicated ratios of protein and charged glucose sulfate in DSCS NP in 50% PBS for 20 min.

Example 3—Activity and Stability of SDF-1a Nanoparticles and VEGF Nanoparticles Migration Assay Protocol:

A Jurkat cell migration assay was used to determine the chemotaxis assay activity of SDF-1α. A previously described procedure was followed. (See, e.g., Yin, T. et al. SDF-1 alpha in glycan nanoparticles exhibits full activity and reduces pulmonary hypertension in rats. *Biomacromolecules* 2013, 14 (11), 4009-20).

Endothelial Cell Proliferation Assay Protocol:

This assay was used to determine the activity of VEGF, for which a previously described procedure was followed. (See, e.g., Lauten, E. et al. Nanoglycan complex formulation extends VEGF retention time in the lung. *Biomacromolecules* 2010, 11 (7), 1863-72). Human pulmonary artery endothelial cells (HPAECs) were used for the assay, and a Cell Proliferation Assay kit (CellTiter 96) was used for estimation of cell proliferation.

Figure 8A:
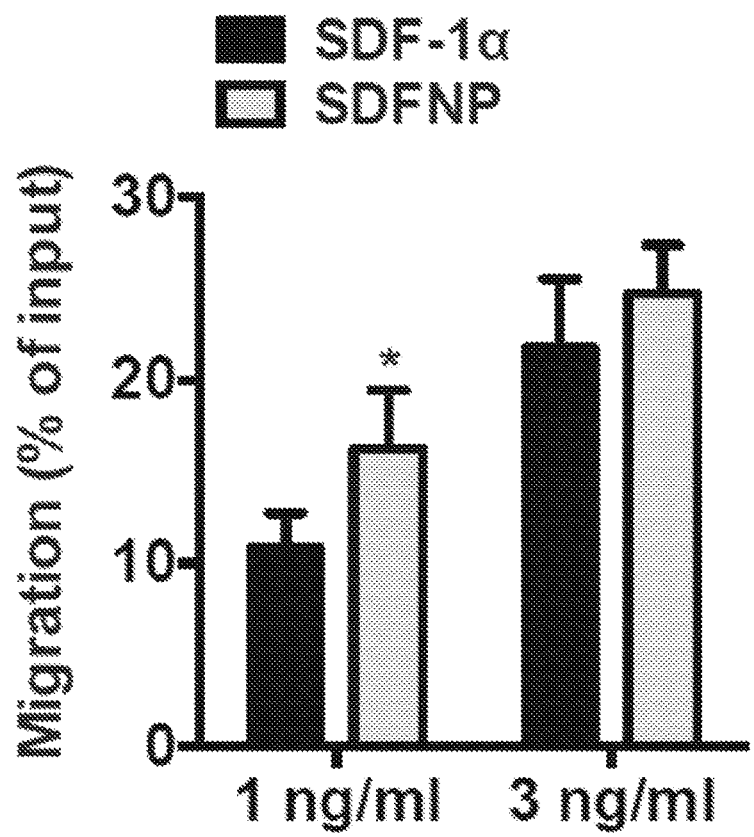
FIG. 8A is a bar graph showing chemotactic activities of SDF-1α and SDFNP were examined by Jurkat cell migration assay at SDF-1α concentrations of 1 ng/ml and 3 ng/ml. SDF-1α (black bars) and SDFNP (gray bars) samples were diluted in 2.5% mannitol and incubated at 37° C. for up to 24 days. At the indicated time points, aliquots were removed and used in migration assays. An SDF-1α stock solution (kept at 4° C.) was used as the control, and the migration assays were performed at an SDF-1α concentration of 3 ng/ml. Data are presented as the mean±SD of four aliquots from two separately prepared samples, * p<0.05 compared to SDF-1α sample in the same group.

Activity and Stability of SDFNP:

To examine the chemotactic activity of NP-incorporated SDF-1α (SDFNP), a Jurkat cell migration assay was carried out. SDF-1α, in free or nanoparticulate forms, was diluted to concentrations of 1 and 3 ng/ml in a migration medium and used for the migration assay. As shown in FIG. 8A, at both SDF-1α concentrations analyzed, the migration activities of free SDF-1α and SDF-1α nanoparticles were similar, indicating that the NP incorporation did not affect the chemotactic activity of SDF-1α.

Figure 8B:
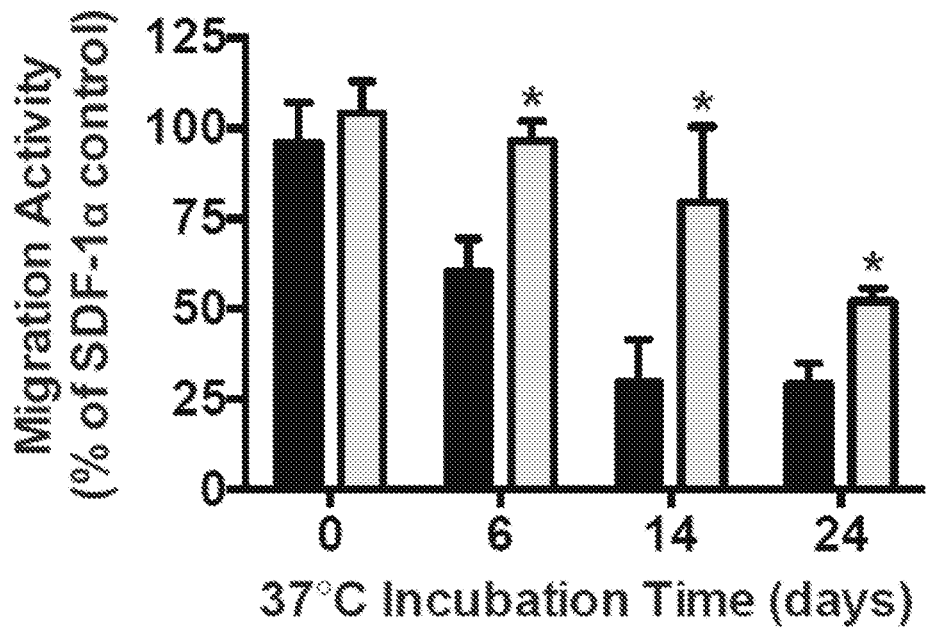
FIG. 8B shows a migration assay of thermal stabilities of SDF-1α and SDFNP. SDF-1α (black bars) and SDFNP (gray bars) samples that were diluted in 2.5% mannitol and incubated at 37° C. for up to 24 days. At the indicated time points, aliquots were removed and used in migration assays. An SDF-1α stock solution (kept at 4° C.) was used as the control, and the migration assays were performed at an SDF-1α concentration of 3 ng/ml. Data are presented as the mean±SD of four aliquots from two separately prepared samples, * p<0.05 compared to SDF-1α sample in the same group.

To determine the thermal stability of the protein nanoparticles, free SDF-1α and SDF-1α nanoparticles (SDF NP) were diluted in 2.5% mannitol and incubated at 37° C. for up to 24 days. Aliquots were removed at various times and analyzed by migration assays. As shown in FIG. 8B, after 6, 14, and 24 days incubation at 37° C., the activity of SDF-1α was 61±9%, 29±12%, and 29±5%, respectively, while the activity of SDF NP were 96±5%, 80±20%, and 52±4%, respectively. Thus, the thermal stability of SDF-1α was improved by incorporation into DSCS nanoparticles. Studies have shown that binding to heparin protects SDF-1α from protease degradation (See e.g., Sadir, R. et al. Heparan sulfate/heparin oligosaccharides protect stromal cell-derived factor-1 (SDF-1)/CXCL12 against proteolysis induced by CD26/dipeptidyl peptidase IV *J. Biol. Chem.* 2004, 279, (42), 43854-60; and Takekoshi, T. et al. A locked, dimeric CXCL12 variant effectively inhibits pulmonary metastasis of CXCR4-expressing melanoma cells due to enhanced serum stability. *Mol. Cancer Ther.* 2012, 11, (11), 2516-25).

Figure 9A:
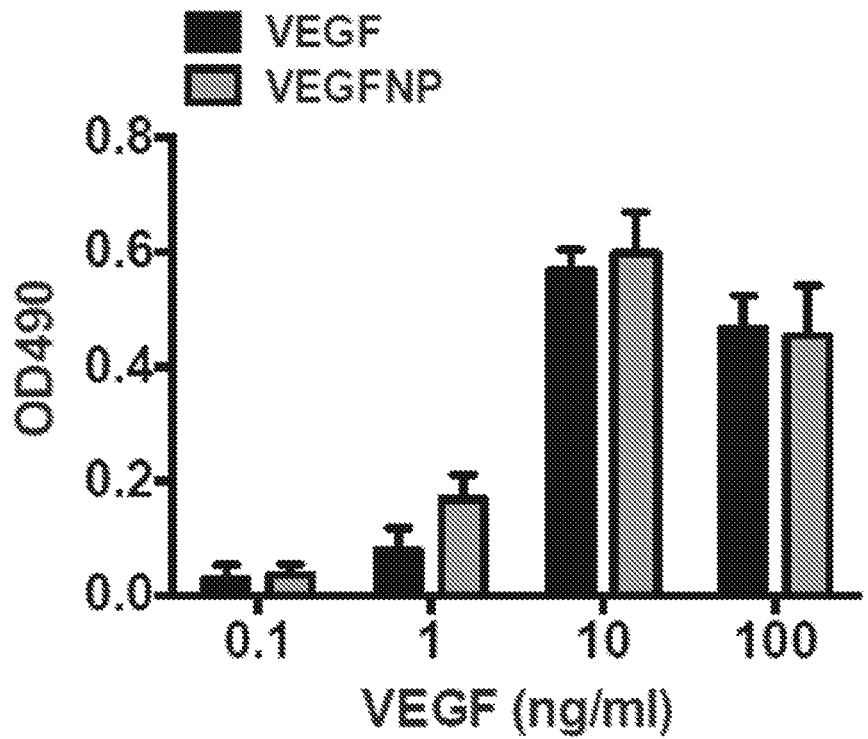
FIG. 9A is a bar graph showing Activities of VEGF and VEGF NP on pulmonary artery endothelial cell proliferation were examined at the indicated concentrations and measured by a colorimetric cell proliferation assay. OD490 indicates the level of cell proliferation. A VEGF stock solution kept at 4° C. was used as control. Data represent mean values of two 37° C. incubation samples run in triplicate in the proliferation assay.
Figure 9B:
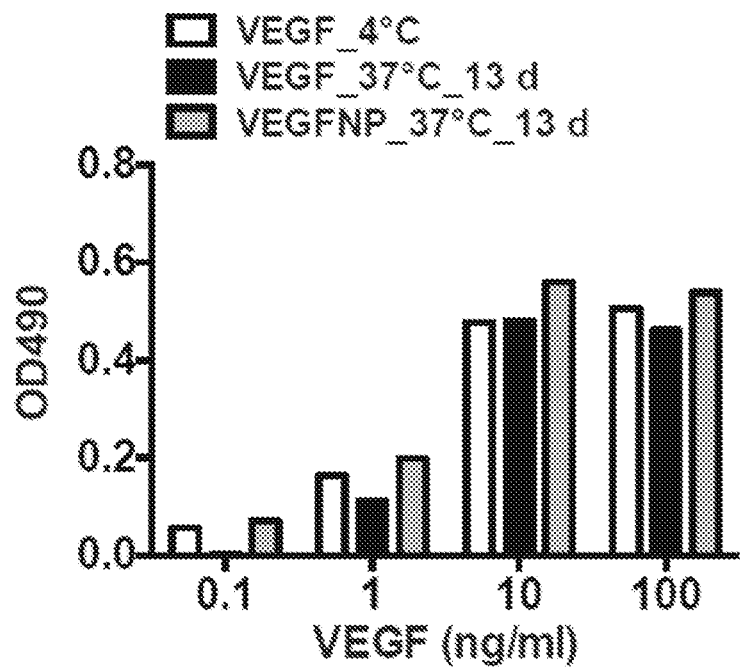
FIG. 9B is a bar graph showing thermal stability of VEGF and VEGF NP, the samples were diluted in 2.5% mannitol to 55 μg/ml and incubated at 37° C. At day 13, aliquots were removed from the incubation samples, and subjected to endothelial cell proliferation assay. Data represent mean values of two 37° C. incubation samples run in triplicate.
Figure 9C:
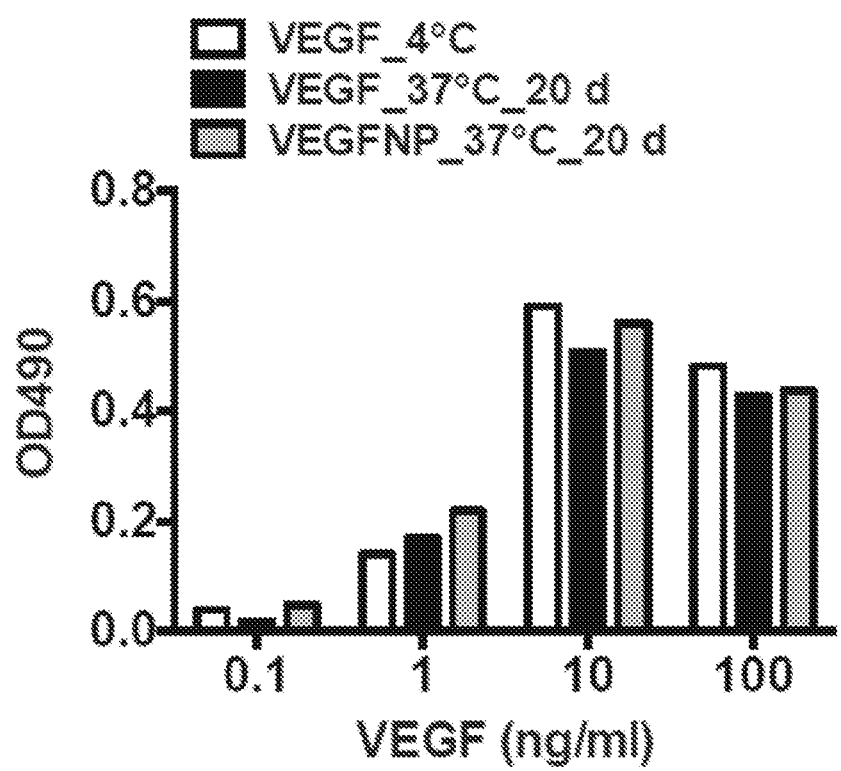
FIG. 9C is a bar graph showing stability of VEGF and VEGF NP, the samples were diluted in 2.5% mannitol to 55 μg/ml and incubated at 37° C. At day 20, aliquots were removed from the incubation samples, and subjected to endothelial cell proliferation assay. Data represent mean values of two 37° C. incubation samples run in triplicate.

Activity and Stability of VEGF NP:

The activity of VEGF was examined by an endothelial cell proliferation assay. As shown in FIG. 9A, NP-incorporated VEGF (VEGF NP) had similar activity as VEGF, which was consistent with a previous finding using VEGF NP made by an entrapment method (See, e.g., Lauten, E. et al, Nanoglycan complex formulation extends VEGF retention time in the lung. Biomacromolecules 2010, 11 (7), 1863-72). To compare the thermal stability of VEGF and VEGF NPs, the samples were incubated at 37° C. for up to 20 days. The activities of the samples were analyzed at various incubation times, and compared with a VEGF stock (control) kept at 4° C. The activities of the samples at day 13 and day 20 incubations are shown in FIG. 9B and FIG. 9C, respectively.

The results show that both VEGF and VEGF NP retained full activity after incubation at 37° C. for 20 days, indicating that the free form of VEGF is unusually thermally stable and the 20-day incubation at 37° C. did not differentiate the stability between VEGF and VEGF NP. This result is consistent with a previous study using a differential scanning calorimetry method to determine the thermal stability of VEGF. (See, e.g., Huang, M et al. Polyelectrolyte complexes stabilize and controllably release vascular endothelial growth factor. Biomacromolecules 2007, 8, (5), 1607-14; and Muller, Y et al. The cystine knot promotes folding and not thermodynamic stability in vascular endothelial growth factor. *J. Biol. Chem.* 2002, 277, (45), 43410-6, wherein it was found that VEGF has an unusually high melting temperature of 107° C. or 108° C., indicating a very high thermal stability). Incorporating VEGF into a DSCS nanoparticle further increases the melting temperature to over 115° C., indicating that the thermal stability of VEGF is further enhanced by incorporation into DSCS NPs.

Example 4—Crosslinking DSCS Nanoparticles

Figure 15:
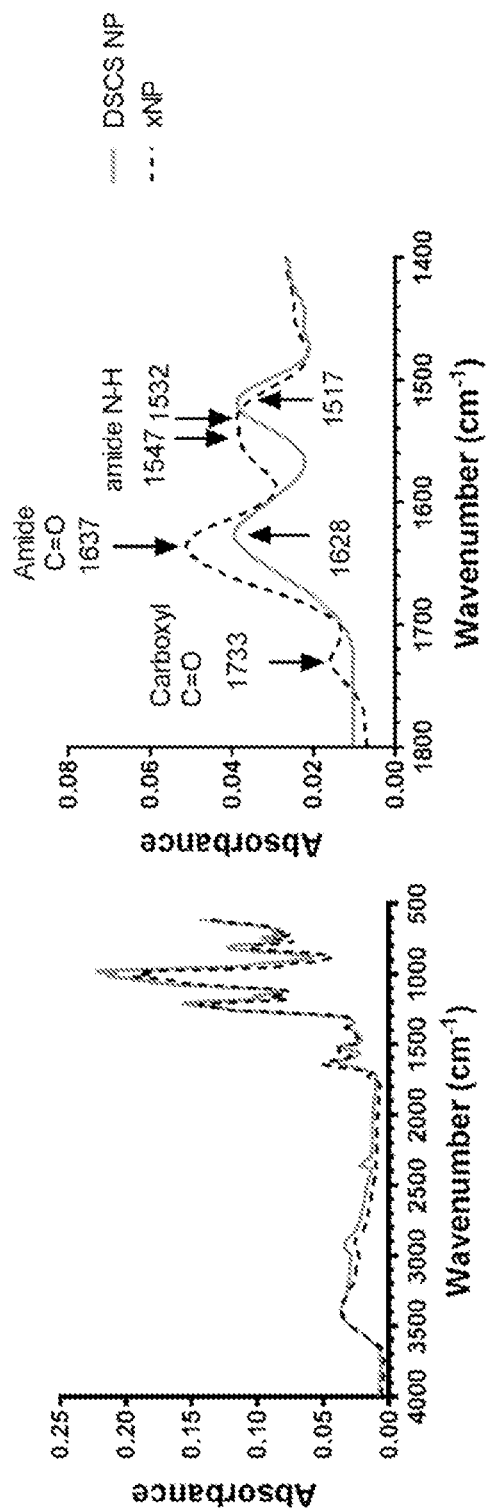
FIG. 15 is a Fourier transform infrared (FTIR) spectra of DSCS nanoparticles before crosslinking (DSCS NPs) and after crosslinking (xNP).

The DSCS nanoparticles were covalently modified by crosslinking the chitosan in the core of the particle with a dicarboxylic acid. In this method, DSCS NPs were suspended in HEPES [4-(2-hydroxyethyl)-1-piperazineethanesulfonic acid] buffered water at pH 7.0. The crosslinking reaction was carried out by mixing the NPs with a short chain dicarboxylic acid (e.g., glutaric acid, malic acid, succinic acid, or tartaric acid, 5-30 mM), 1-ethyl-3-(3-dimethylaminopropyl) carbodiimide (EDC, 20-100 mM)), and N-hydroxysuccinimide (NHS, 20-100 mM) for 16 h at 25° C. The particles were precipitated by centrifugation at 15,000×g for 15 min, washed with DPBS, and resuspended in 3×DPBS (3-fold high concentration of DPBS) for salt-resistance selection. After 3 h incubation, aggregates in the suspension were precipitated by centrifugation at 200×g for 15 min, and the remaining particles were precipitated by a centrifugation at 15,000×g for 15 min. The particles were then resuspended in DPBS, and filtered through PVDF membranes with pore size of 0.22 micrometer. The resulting particles are referred to as crosslinked NP (xNP). The crosslinking reaction results in amide bond formation between the amine groups in chitosan and the carboxyl groups in the dicarboxylic acid, which bridges chitosan together in the core of the particle. The formation of new amide in the crosslinked NP is demonstrated in Fourier transform infrared (FTIR) spectra shown FIGS. 12 and 15.

Properties of Crosslinked DSCS NPs (xNPs)

Figure 13:
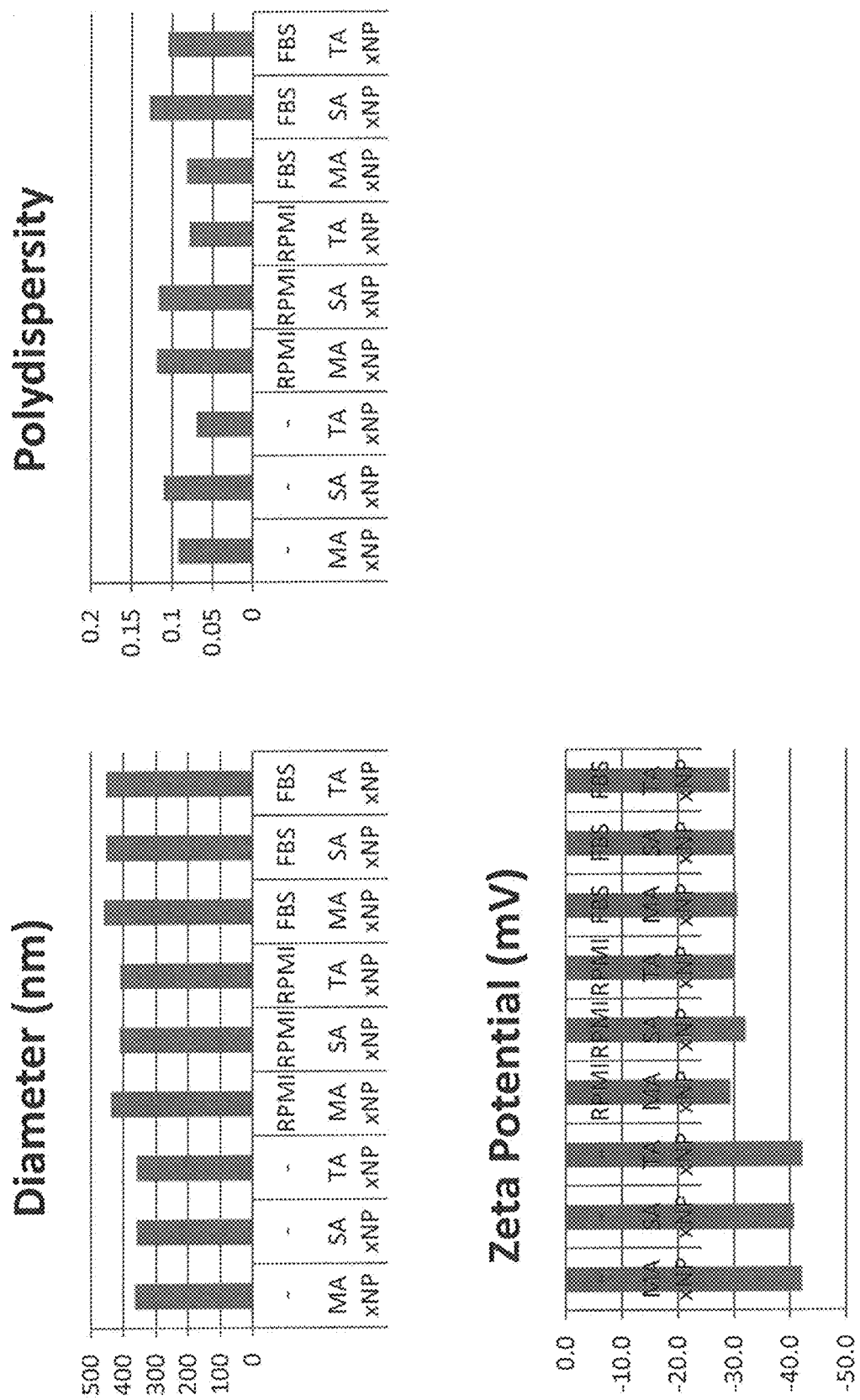
FIG. 13 is a bar graph showing stability of crosslinked DSCS NPs. Crosslinked NPs, MA xNP, SA xNP, or TA xNP, were incubated with fetal bovine serum (FBS) or RPMI 1640 plus 10% FBS (RPMI) at 25° C. for 16 h. Particles were then washed and suspended in PBS, and their size and zeta potential were determined. Data indicate that crosslinked DSCS NPs are stable in complete serum or cell culture medium.
Figure 16A:
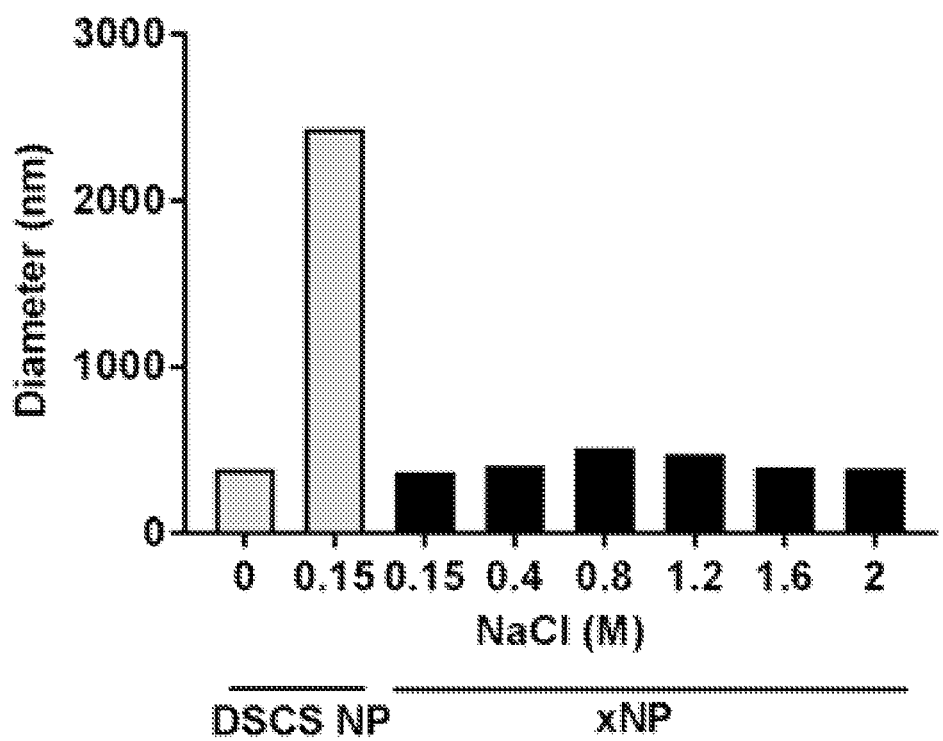
FIG. 16A is a bar graph showing particle diameter of DSCS NP and crosslinked NP (xNP) in NaCl solutions after incubation at 25° C. for 16 h. Data indicate that DSCS NP aggregates in physiological saline (0.15 M NaCl), while xNP is resistant to NaCl concentration up to 2 M.
Figure 16B:
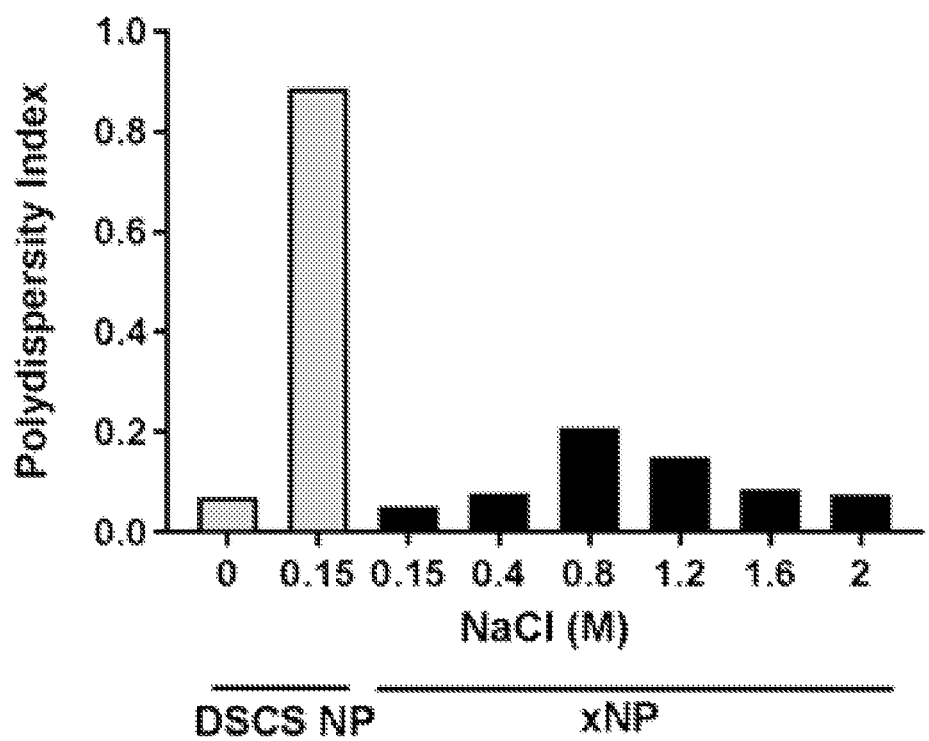
FIG. 16B is a bar graph showing polydispersity index of DSCS NP and crosslinked NP (xNP) in NaCl solutions. Dramatic increase in polydispersity index was found in DSCS NP after incubation in 0.15 M NaCl, which indicates severe aggregation and heterogeneity of the particle population. In comparison, xNP maintained its homogeneity throughout the incubation in high salt solutions.
Figure 17:
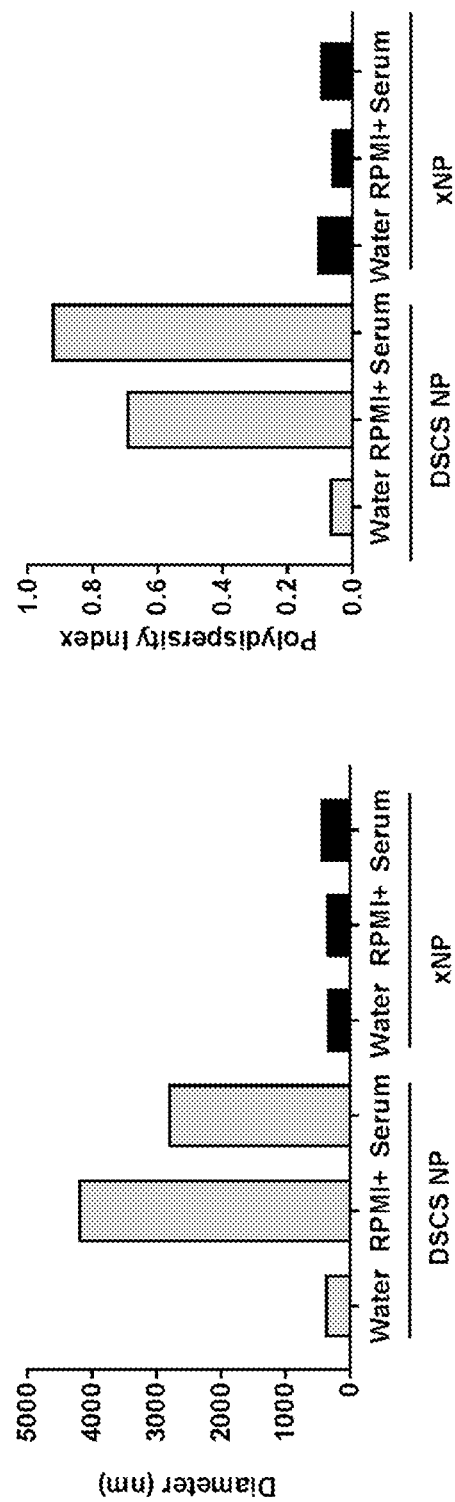
FIG. 17 contains bar graphs showing stability of DSCS NP and crosslinked NP (xNP) in complete cell culture medium, RPMI 1640 plus 10% FBS (RPMI+) and fetal bovine serum (serum). Data indicate that DSCS NP aggregates in these media but crosslinked NP was not affected.

The crosslinked DSCS NP (xNP) gained remarkable salt-stability as compared to that of un-crosslinked particles. As shown in FIGS. 13, 16 and 17, the particle size and homogeneity (polydispersity index) of xNP was not altered after incubation in up to 2 M NaCl solutions, while un-crosslinked DSCS NP aggregates in 0.15 M NaCl solution. Similarly, xNP was stable in fetal bovine serum (serum) and a complete cell culture medium, RPMI 1640 plus 10% FBS (RPMI+), while DSCS NP aggregated in these media.

Figure 18:
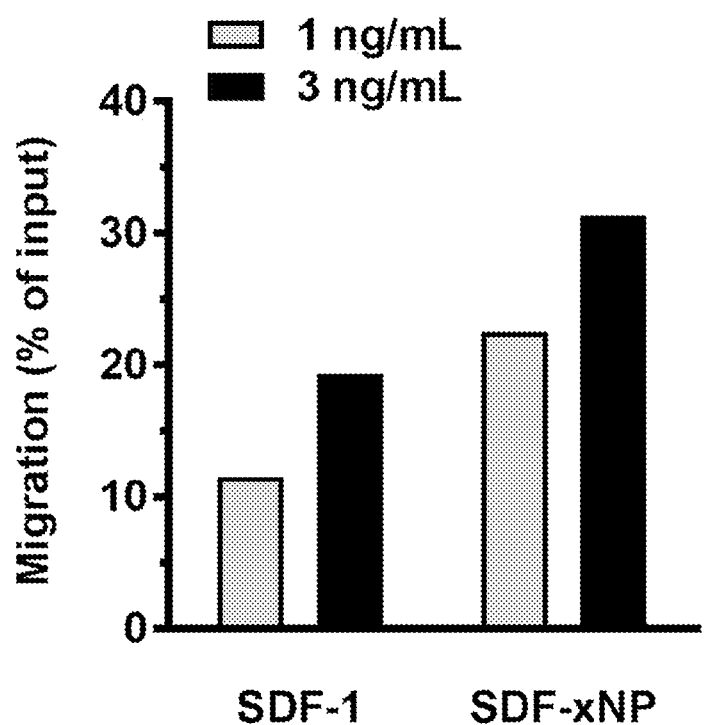
FIG. 18 is a bar graph showing chemotactic activity of SDF-1α before (SDF-1) and after incorporation into crosslinked DSCS NP (SDF-xNP). Data indicate that SDF-1α exhibits similar or slightly greater activity after incorporation into crosslinked NP.
Figure 19:
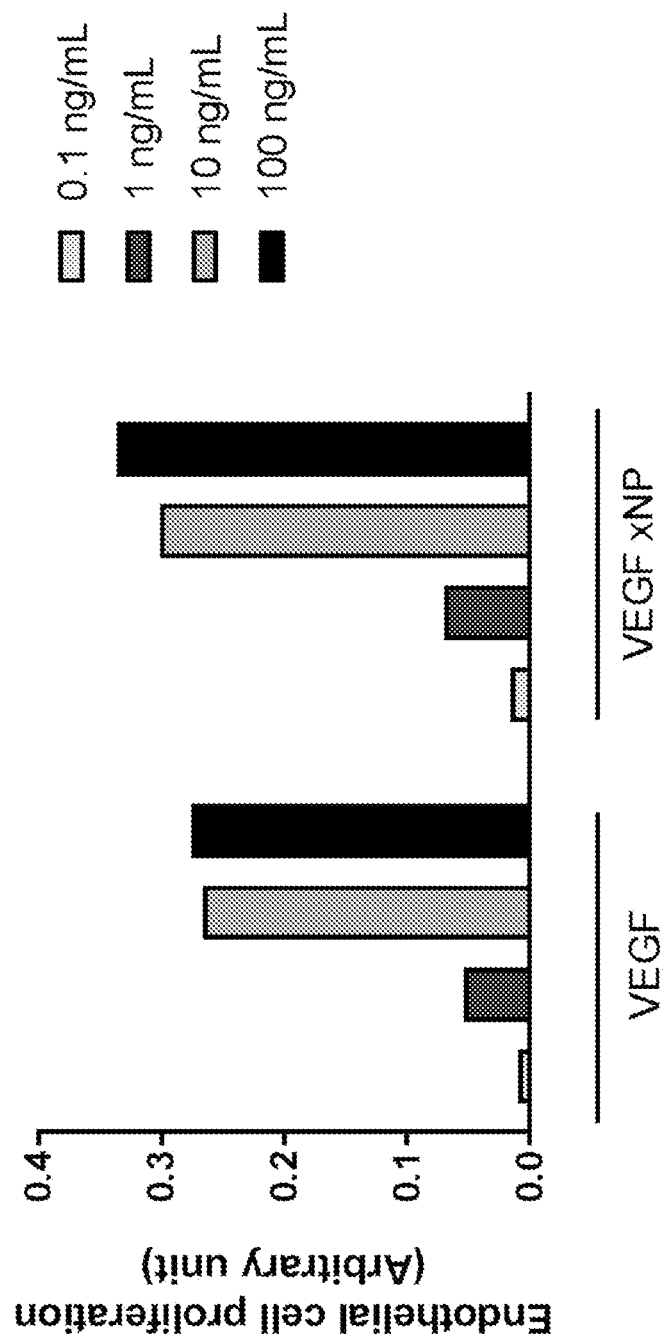
FIG. 19 is a bar graph showing proliferation activity of VEGF before (VEGF) and after incorporation into crosslinked DSCS NP (VEGF xNP). Data indicate VEGF has similar activity before and after incorporation into crosslinked NP.

The xNP has similar particle size and the surface property as that of the DSCS NP, since the crosslinking reaction occurs in the core of the particle. The xNP allows heparin-binding proteins to be incorporated in a similar manner as DSCS NP (FIG. 14 and Table 4), and the bound proteins exhibit full or enhanced biological activity. See FIGS. 18 and 19.

Figure 14:
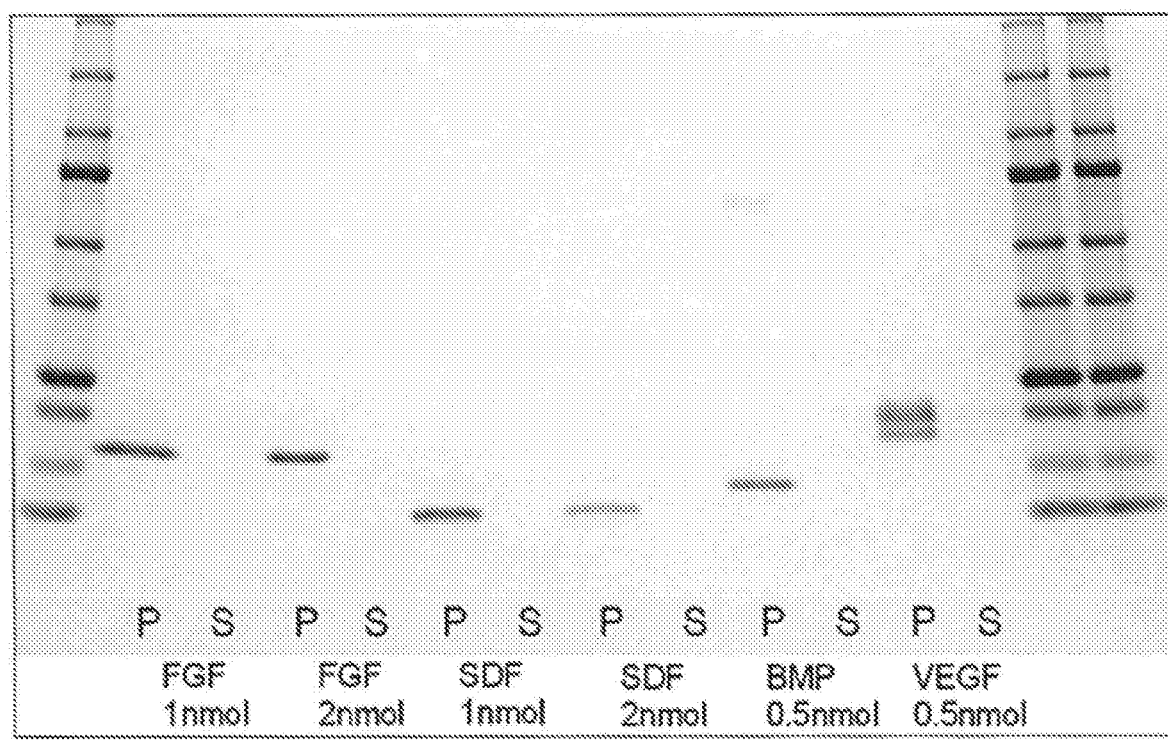
FIG. 14 is a plot showing incorporation of proteins into crosslinked DSCS NPs (xNPs). Indicated amount of FGF-2, SDF-1α, BMP-2, or VEGF were mixed with xNPs containing 100 nmol charged glucose sulfate units (Gluc-SO$^{3-}$) in PBS for 20 min. Un-incorporated protein was separated from particles by centrifugation, and resulted pellet (P) and supernatant (S) fractions were analyzed on SDS gel. Incorporation efficiencies were estimated based on densitometry analysis of gel bands. Protein-incorporated xNPs were then lyophilized and stored at −80° C. Particles size and zeta potential of protein-incorporated xNPs were determined after reconstitution of the NPs in PBS. Data show that incorporation efficiencies of the examined growth factors to xNP were 95-100%, particle size and zeta potential of xNPs were not significantly altered at indicated protein loading ratios, and the particles were stable throughout incorporation and storage process.

Incorporation of Proteins into Crosslinked Nanoparticles:
FIG. 14 and Table 4 show incorporation of proteins into crosslinked DSCS NPs (xNPs).

TABLE 4

Incorporation of proteins into crosslinked DSCS NPs

| Protein | Protein:Gluc-SO$_3^-$ (nmol:nmol) | Incorp. Efficiency (%) | Diameter (nm) | Polydisp. Index | Zeta Potential (mV) |
|---|---|---|---|---|---|
| None |  |  | 369 | 0.61 | −45.1 |
| FGF-2 | 1:100 | 100 | 351 | 0.155 | −48.8 |
| FGF-2 | 2:100 | 100 | 423 | 0.382 | −35.6 |
| SDF-1a | 1:100 | 100 | 330 | 0.123 | −40.6 |
| SDF-1a | 2:100 | 100 | 324 | 0.233 | −35.9 |
| BMP-2 | 0.5:100 | 100 | 343 | 0.117 | −46.9 |
| VEGF | 0.5:100 | 95 | 323 | 0.114 | −45.1 |

Protocol:

Indicated amount of FGF-2, SDF-1α, BMP-2, or VEGF were mixed with xNPs containing 100 nmol charged glucose sulfate units (Gluc-SO$_3^-$) in PBS for 20 min. Un-incorporated protein was separated from particles by centrifugation, and resulted pellet (P) and supernatant (S) fractions were analyzed on SDS gel (as shown in FIG. 14). Incorporation efficiencies were estimated based on densitometry analysis of gel bands. Protein-incorporated xNPs were then lyophilized and stored at −80° C. Particles size and zeta potential of protein-incorporated xNPs were determined after reconstitution of the NPs in PBS. Data show that incorporation efficiencies of the examined growth factors to xNP were 95-100%, particle size and zeta potential of xNPs were not significantly altered at indicated protein loading ratios, and the particles were stable throughout incorporation and storage process.

Figure 20:
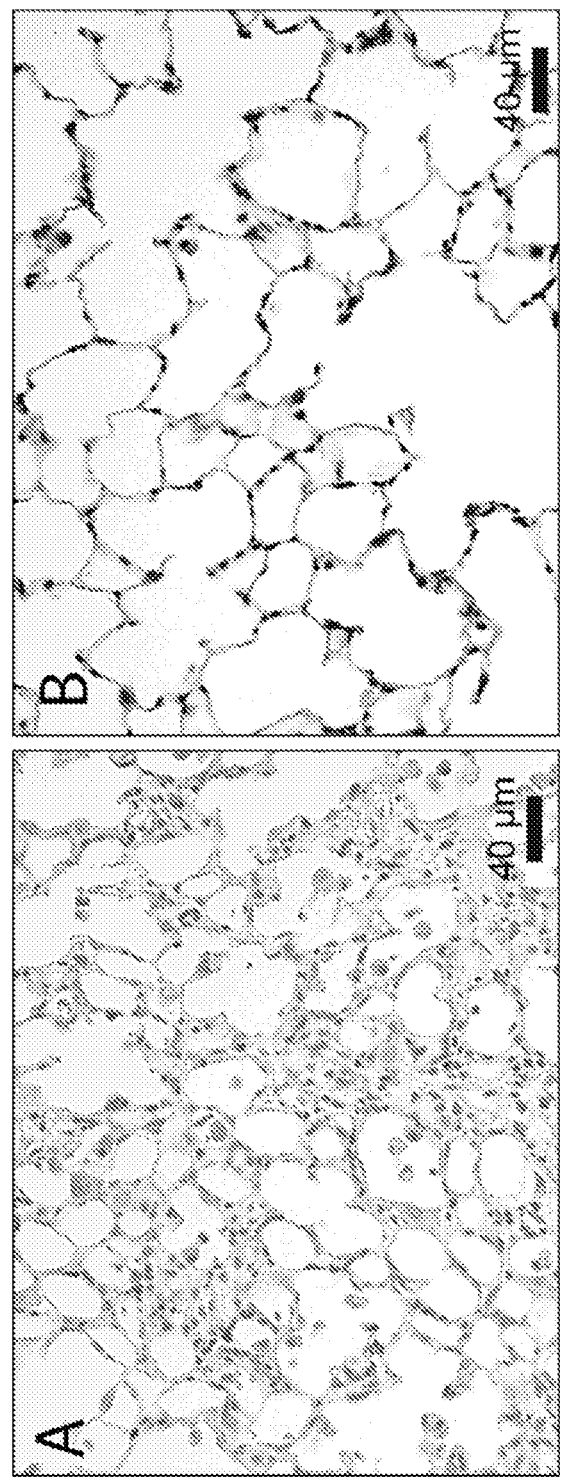
FIG. 20 shows hematoxylin and eosin-stained lung sections obtained from rats that received aerosolization of DSCS NP (panel A) or crosslinked NP (xNP, panel B). Both rats had been injected with monocrotaline which causes pulmonary endothelial injury and pulmonary hypertension, and received cyclosporine as an immunosuppressant for stem cell therapy. Under these severe conditions, DSCSNP could cause severe pulmonary inflammation/fibrosis, while xNP is harmless.

In Vivo Properties xNP does not aggregate in body fluid or a semi-fluid body surface. This property prevents inflammatory responses to the particles, especially in the setting of inflammatory diseases. FIG. 20 shows an example of the difference. The rats used for the study were injected with monocrotaline, which causes pulmonary endothelial injury and pulmonary hypertension. In addition, the rats received daily cyclosporine, an immunosuppressant used for stem cell therapy. When DSCS NPs and xNPs were aerosolized in the lungs of these rats, inflammation and fibrosis were found in some of the DSCS NP treated rats, but not in xNP treated rats. These results suggest that xNP may be superior to DSCS NP for in vivo delivery purposes.

Characterization of Crosslinked Nanoparticles

Figure 12:
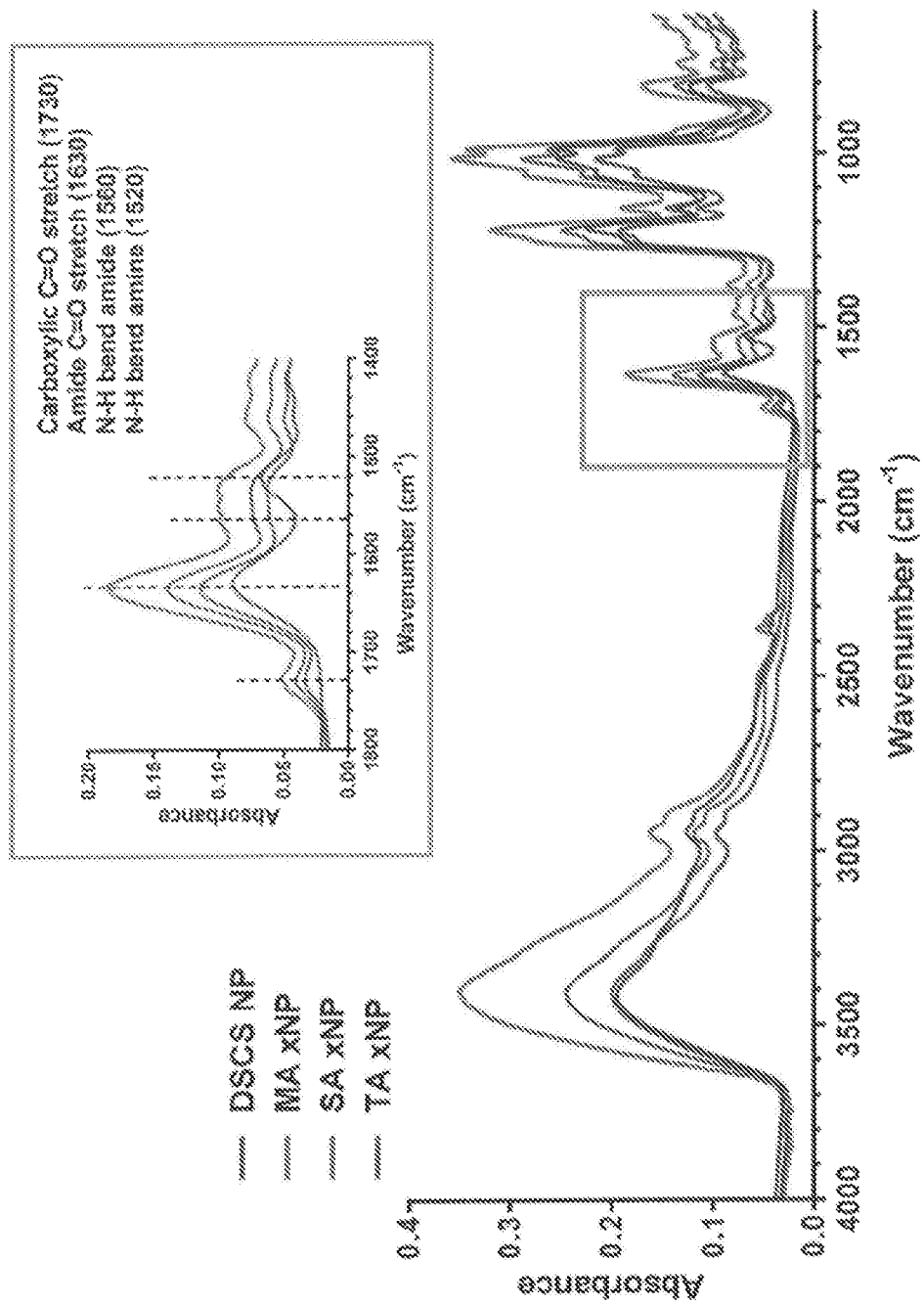
FIG. 12 shows Fourier transform infrared (FTIR) spectra of dextran sulfate and chitosan nanoparticle (DSCS NP) before and after crosslinking (xNP). Data indicate new amide bond formation in crosslinked NP and residue of carboxylic group that were introduced by dicarboxylic acid.

Fourier transform infrared spectra of dextran sulfate and chitosan nanoparticles (DSCS NP) and its crosslinked derivatives MA xNP, SA xNP, and TA xNP is shown in FIG. 12. Data show amide bond formation in crosslinked NPs.

Stability of Crosslinked Nanoparticles

Stability of crosslinked DSCS NPs is demonstrated in FIG. 13. Crosslinked NPs, MA xNP, SA xNP, or TA xNP, were incubated with fetal bovine serum (FBS) or RPMI 1640 plus 10% FBS (RPMI) at 25° C. for 16 h. Particles were then washed and suspended in PBS, and their size and zeta potential were determined. Data indicate that crosslinked DSCS NPs are stable in complete serum or cell culture medium.

The modified DSCS NPs are stable in high salt solutions and various physiological fluids (including plasma), and can be easily loaded with heparin-binding proteins for therapeutic purposes. The particle contains calcium ion instead of zinc ion, which is more compatible for injection onto blood.

Example 5—Intratracheal Aerosolization and Analysis of Lung Tissue for SDF-1α Content (In Vivo Retention Time of SDF NP)

Sprague Dawley male rats at body weight of 200-225 g were purchased from Charles River Laboratories, and were acclimated for 4 days in our animal facility. Animal studies were performed according to protocols approved by the Harvard Medical Area Standing Committee on Animals.

Intratracheal aerosolization of SDF-1α or SDF nanoparticles as well as the analysis of SDF-1α content in the lung was performed according to a previously described procedure. (See, e.g., Yin, T. et al, SDF-1alpha in glycan nanoparticles exhibits full activity and reduces pulmonary hypertension in rats. *Biomacromolecules* 2013, 14 (11), 4009-20). Briefly, SDF-1α or SDF nanoparticles with 12 µg SDF-1α content were diluted in 50% PBS in a volume of 0.25 ml and aerosolized into the lungs of rats with a MicroSprayer Aerosolizer from Penn-Century. At 0, 16, 48, and 72 h after the aerosolization, rat lung tissue was harvested and frozen in liquid nitrogen. The tissue was homogenized, and the protein concentrations in the homogenate supernatants were determined by the BCA protein assay. SDF-1α concentrations in the supernatants were determined by ELISA using reagents from R&D systems following the manufacturer's instructions.

Figure 10:
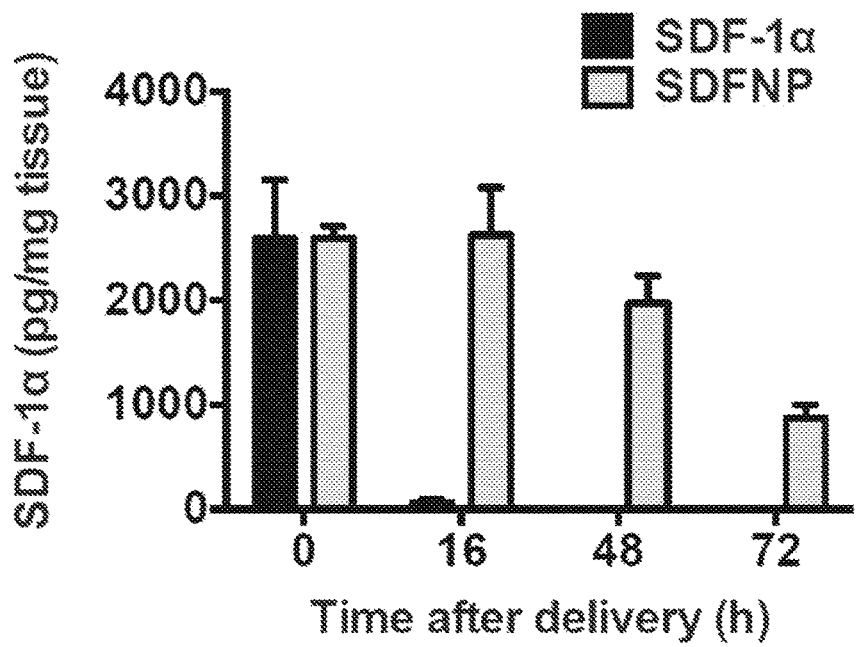
FIG. 10 is a bar graph showing Retention time of SDF-1α and SDFNP in the lungs of rats. SDF-1α and SDFNP (12 μg SDF-1α content) were aerosolized into the rat lungs. At the indicated time points, lung tissues were harvested and homogenized. The concentrations of SDF-1α in the homogenates were determined by ELISA. Data represent mean±SEM from tissue obtained from 4 rats.

As shown in FIG. 10, SDF-1α content in the lung tissue exposed to the free form of SDF-1α was nearly undetectable 16 h after the aerosolization (~2% remaining), but remained detectable in the lungs exposed to SDF NP at 100%, 76%, and 34% of initial values at 16 h, 48 h, and 72 h after delivery, respectively.

REFERENCES

1. Leader B, Baca Q J, Golan D E. Protein therapeutics: a summary and pharmacological classification. *Nat. Rev. Drug Discov.* January 2008; 7(1):21-39.
2. Kontermann R E. Strategies for extended serum half-life of protein therapeutics. *Curr. Opin. Biotechnol.* December 2011; 22(6):868-876.
3. Chen Y, Siddalingappa B, Chan P H, Benson H A. Development of a chitosan-based nanoparticle formulation for delivery of a hydrophilic hexapeptide, dalargin. *Biopolymers*. 2008; 90(5):663-670.
4. Sarmento B, Ribeiro A, Veiga F, Ferreira D, Neufeld R. Oral bioavailability of insulin contained in polysaccharide nanoparticles. *Biomacromolecules*. October 2007; 8(10): 3054-3060.
5. Huang M, Vitharana S N, Peek L J, Coop T, Berkland C. Polyelectrolyte complexes stabilize and controllably release vascular endothelial growth factor. *Biomacromolecules*. May 2007; 8(5):1607-1614.
6. Drogoz A, Munier S, Verrier B, David L, Domard A, Delair T. Towards biocompatible vaccine delivery systems: interactions of colloidal PECs based on polysaccharides with HIV-1 p24 antigen. *Biomacromolecules*. February 2008; 9(2):583-591.
7. Huang M, Berkland C. Controlled release of repifermin from polyelectrolyte complexes stimulates endothelial cell proliferation. *J. Pharm. Sci.* January 2009; 98(1):268-280.
8. Sharma S, Mukkur T K, Benson H A, Chen Y. Enhanced immune response against pertussis toxoid by IgA-loaded chitosan-dextran sulfate nanoparticles. *J. Pharm. Sci.* January 2012; 101(1):233-244.
9. Lauten E H, VerBerkmoes J, Choi J, et al. Nanoglycan complex formulation extends VEGF retention time in the lung. *Biomacromolecules*. Jul. 12, 2010; 11(7):1863-1872.
10. Yin T, Bader A R, Hou T K, et al. SDF-1 alpha in glycan nanoparticles exhibits full activity and reduces pulmonary hypertension in rats. *Biomacromolecules*. Nov. 11, 2013; 14(11):4009-4020.
11. Ricketts C R. Dextran sulphate—a synthetic analogue of heparin. *Biochem. J.* April 1952; 51(1):129-133.
12. Xu D, Esko J D. Demystifying heparan sulfate-protein interactions. *Annu. Rev. Biochem.* 2014; 83:129-157.
13. Gallagher J. Fell-Muir Lecture: Heparan sulphate and the art of cell regulation: a polymer chain conducts the protein orchestra. *Int J Exp Pathol*. August 2015; 96(4): 203-231.
14. Ori A, Wilkinson M C, Fernig D G. A systems biology approach for the investigation of the heparin/heparan sulfate interactome. *J. Biol. Chem.* Jun. 3, 2011; 286(22): 19892-19904.
15. Bader A R, Li T, Wang W, Kohane D S, Loscalzo J, Zhang Y Y. Preparation and characterization of SDF-1 alpha-chitosan-dextran sulfate nanoparticles. *J Vis Exp*. 2015(95):52323.
16. Ellis H A, Walton K W. The estimation and recovery of dextran sulphates in biological fluids. *J. Clin. Pathol.* September 1959; 12:467-472.
17. Grant A C, Linhardt R J, Fitzgerald G L, Park J J, Langer R. Metachromatic activity of heparin and heparin fragments. *Anal. Biochem.* February 1984; 137(1):25-32.
18. Mendelovits A, Prat T, Gonen Y, Rytwo G. Improved colorimetric determination of chitosan concentrations by dye binding. *Appl Spectrosc*. August 2012; 66(8):979-982.
19. Muzzarelli R A. Colorimetric determination of chitosan. *Anal. Biochem.* Jul. 1, 1998; 260(2):255-257.
20. Stebler J, Spieler D, Slanchev K, et al. Primordial germ cell migration in the chick and mouse embryo: the role of the chemokine SDF-1/CXCL12. *Dev. Biol*. Aug. 15, 2004; 272(2):351-361.
21. Sharma M, Afrin F, Satija N, Tripathi R P, Gangenahalli G U. Stromal-derived factor-1/CXCR4 signaling: indispensable role in homing and engraftment of hematopoietic stem cells in bone marrow. *Stem Cells Dev.* June 2011; 20(6):933-946.
22. Ghadge S K, Muhlstedt S, Ozcelik C, Bader M. SDF-1 alpha as a therapeutic stem cell homing factor in myocardial infarction. *Pharmacol. Ther*. January 2011; 129 (1):97-108.
23. Amara A, Lorthioir O, Valenzuela A, et al. *Stromal cell-derived factor-1 alpha associates with heparan sulfates through the first beta-strand of the chemokine*. J. Biol. Chem. Aug. 20, 1999; 274(34):23916-23925.
24. Sadir R, Baleux F, Grosdidier A, Imberty A, Lortat-Jacob H. Characterization of the stromal cell-derived factor-1 alpha-heparin complex. *J. Biol. Chem.* Mar. 16, 2001; 276(11):8288-8296.
25. Fermas S, Gonnet F, Sutton A, et al. Sulfated oligosaccharides (heparin and fucoidan) binding and dimerization of stromal cell-derived factor-1 (SDF-1/CXCL 12) are coupled as evidenced by affinity CE-MS analysis. *Glycobiology*. December 2008; 18(12):1054-1064.
26. Ferrara N. Molecular and biological properties of vascular endothelial growth factor. *J Mol Med* (Berl). July 1999; 77(7):527-543.
27. Fairbrother W J, Champe M A, Christinger H W, Keyt B A, Starovasnik M A. Solution structure of the heparin-binding domain of vascular endothelial growth factor. *Structure*. May 15, 1998; 6(5):637-648.
28. Robinson C J, Mulloy B, Gallagher J T, Stringer S E. VEGF165-binding sites within heparan sulfate encompass two highly sulfated domains and can be liberated by K5 lyase. *J. Biol. Chem*. Jan. 20, 2006; 281(3):1731-1740.
29. Zhao W, McCallum S A, Xiao Z, Zhang F, Linhardt R J. Binding affinities of vascular endothelial growth factor (VEGF) for heparin-derived oligosaccharides. *Biosci Rep.* February 2012; 32(1):71-81.
30. DiGabriele A D, Lax I, Chen D I, et al. Structure of a heparin-linked biologically active dimer of fibroblast growth factor. *Nature*. Jun. 25, 1998; 393(6687):812-817.
31. Faham S, Hileman R E, Fromm J R, Linhardt R J, Rees D C. Heparin structure and interactions with basic fibroblast growth factor. *Science*. Feb. 23, 1996; 271(5252): 1116-1120.
32. Schlessinger J, Plotnikov A N, Ibrahimi O A, et al. Crystal structure of a ternary FGF-FGFR-heparin complex reveals a dual role for heparin in FGFR binding and dimerization. *Mol. Cell*. September 2000; 6(3):743-750.
33. Ruppert R, Hoffmann E, Sebald W. Human bone morphogenetic protein 2 contains a heparin-binding site which modifies its biological activity. *Eur. J. Biochem*. Apr. 1, 1996; 237(1):295-302.
34. Vallejo L F, Rinas U. Folding and dimerization kinetics of bone morphogenetic protein-2, a member of the transforming growth factor-beta family. *FEBS J*. January 2013; 280(1):83-92.
35. Zou S, Magura C E, Hurley W L. Heparin-binding properties of lactoferrin and lysozyme. *Comp Biochem Physiol B*. December 1992; 103(4):889-895.
36. Morris J, Jayanthi S, Langston R, et al. Heparin-binding peptide as a novel affinity tag for purification of recombinant proteins. *Protein Expr Purif*. October 2016; 126: 93-103.
37. Sadir R, Imberty A, Baleux F, Lortat-Jacob H. Heparan sulfate/heparin oligosaccharides protect stromal cell-derived factor-1 (SDF-1)/CXCL12 against proteolysis induced by CD26/dipeptidyl peptidase IV. *J. Biol. Chem*. Oct. 15, 2004; 279(42):43854-43860.
38. Takekoshi T, Ziarek J J, Volkman B F, Hwang S T. A locked, dimeric CXCL12 variant effectively inhibits pulmonary metastasis of CXCR4-expressing melanoma cells due to enhanced serum stability. *Mol. Cancer Ther*. November 2012; 11(11):2516-2525.
39. Muller Y A, Heiring C, Misselwitz R, Welfle K, Welfle H. The cystine knot promotes folding and not thermodynamic stability in vascular endothelial growth factor. *J. Biol. Chem*. Nov. 8, 2002; 277(45):43410-43416.
40. Delair, T. (2011) Colloidal polyelectrolyte complexes of chitosan and dextran sulfate towards versatile nanocarriers of bioactive molecules. *Eur J Pharm Biopharm* 78, 10-18.
41. Zaman, P., Wang, J., Blau, A., Wang, W., Li, T., Kohane, D. S., Loscalzo, J., and Zhang, Y. Y. (2016) Incorporation of heparin-binding proteins into preformed dextran sulfate-chitosan nanoparticles. *Int J Nanomedicine* 11, 6149-6159.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of making a therapeutic particle, the method comprising:
   i) obtaining a solution comprising a therapeutic protein;
   ii) obtaining a first suspension comprising a particle comprising a negatively charged polysaccharide and a positively charged polysaccharide, wherein the core of the particle comprises the positively charged polysaccharide, wherein the positively charged polysaccharide is covalently crosslinked by a dicarboxylic acid linker in the core of the particle; and
   iii) mixing the solution of the therapeutic protein and the first suspension to obtain a second suspension comprising the therapeutic particle.

2. The method of claim 1, wherein
   the negatively charged polysaccharide comprises a monosaccharide unit having a functional group that is negatively charged at physiological pH; and
   the positively charged polysaccharide comprises a monosaccharide unit having a functional group that is positively charged at physiological pH.

3. The method of claim 2, wherein
   the molar ratio of the therapeutic protein in the solution to the monosaccharide units having the negatively charged functional group within the negatively charged polysaccharide in the particle is from about 0.25:100 to about 3:100; and/or
   the weight ratio of the negatively charged polysaccharide to the positively charged polysaccharide in the particle is from about 3:1 to about 5:1.

4. The method of claim 2, wherein
   the negatively charged polysaccharide comprises a monosaccharide unit having a functional group selected from: carboxylic acid (—C(═O)OH), sulfonic acid (—S(═O)$_2$(OH) or —SO$_3$H), and phosphonic acid (—P(═O)(OH)$_2$); and
   the positively charged polysaccharide comprises a monosaccharide unit having an amino group (—NH$_2$).

5. The method of claim 1, wherein:
   the negatively charged polysaccharide is a glycosaminoglycan or a glycan; and
   the positively charged polysaccharide is a polyglucosamine.

6. The method of claim 5, wherein:
   the negatively charged polysaccharide is selected from heparin, heparan sulfate, chondroitin sulfate, dermatan sulfate, keratan sulfate, hyaluronic acid; and dextran sulfate; and
   the positively charged polysaccharide is a chitosan.

7. The method of claim 1, comprising:
   iv) obtaining a first solution comprising a negatively charged polysaccharide;
   v) obtaining a second solution comprising a positively charged polysaccharide; and
   vi) mixing the first solution and the second solution to obtain the first suspension comprising the particle comprising the negatively charged polysaccharide and the positively charged polysaccharide, wherein the core of the particle comprises the positively charged polysaccharide.

8. The method of claim 7, wherein
   the mixing of the first solution and the second solution in step iii) is followed by addition of an aqueous solution of a metal salt to the mixture; and
   the addition of the aqueous solution of the metal salt to the mixture of step iii) is followed by the addition of an aqueous solution of a sugar alcohol to the mixture.

9. The method of claim 8, wherein the metal salt is a zinc salt, and the sugar alcohol is mannitol.

10. The method of claim 1, comprising mixing the first suspension with a dicarboxylic acid to achieve crosslinking of the positively charged polysaccharide in the core of the particle.

11. The method of claim 1, wherein the therapeutic protein comprises a heparin-binding domain; and the therapeutic protein is non-covalently bound to the negatively charged polysaccharide in the therapeutic particle.

12. The method of claim 1, wherein the therapeutic protein is selected from a growth factor, a cytokine, an antibody, a hormone, a transmembrane protein, and an enzyme.

13. The method of claim 1, wherein the therapeutic protein is selected from stromal cell-derived factor-1α (SDF-1α), vascular endothelial growth factor (VEGF), oncostatin M (OSM), ciliary neurotrophic factor (CNTF), bone morphogenetic protein-2 (BMP-2), basic fibroblast growth factor (FGF-2) and lysozyme.

14. A therapeutic particle comprising a therapeutic protein, a positively charged polysaccharide, and a negatively charged polysaccharide, wherein the particle consists of core and outer shell;
   wherein the core of the particle comprises the positively charged polysaccharide, and the positively charged polysaccharide is covalently crosslinked by a dicarboxylic acid linker in the core of the particle;
   wherein the therapeutic protein in the outer shell is non-covalently bound to the negatively charged polysaccharide in the therapeutic particle; and
   wherein the therapeutic protein is the protein to treat a disease or condition selected from cancer, inflammation, macular degeneration, and pulmonary hypertension.

15. A pharmaceutical composition comprising a therapeutic particle of claim 14, and a pharmaceutically acceptable carrier.

16. A method of treating a disease or condition selected from cancer, inflammation, macular degeneration, and pulmonary hypertension, the method comprising administering to a subject in need thereof a therapeutically effective amount of a therapeutic particle comprising the therapeutic protein according to claim 14.

* * * * *